United States Patent
Vermot-Desroches et al.

(10) Patent No.: US 12,077,597 B2
(45) Date of Patent: Sep. 3, 2024

(54) ANTI-CD5 ANTIBODIES AND METHODS OF USE THEREOF

(71) Applicant: INTERNATIONAL-DRUG-DEVELOPMENT-BIOTECH, Lyons (FR)

(72) Inventors: Claudine Vermot-Desroches, Dardilly (FR); Hélène Rouquette, Paris (FR); Benoît Milcent, Paris (FR)

(73) Assignee: INTERNATIONAL-DRUG-DEVELOPMENT-BIOTECH, Lyons (FR)

( * ) Notice: Subject to any disclaimer, the term of this patent is extended or adjusted under 35 U.S.C. 154(b) by 0 days.

(21) Appl. No.: 17/534,707

(22) Filed: Nov. 24, 2021

(65) Prior Publication Data
US 2023/0159654 A1    May 25, 2023

(51) Int. Cl.
| | | |
|---|---|---|
| *C07K 16/28* | (2006.01) | |
| *A61K 39/00* | (2006.01) | |
| *A61P 35/00* | (2006.01) | |
| *A61P 35/02* | (2006.01) | |

(52) U.S. Cl.
CPC .......... *C07K 16/2896* (2013.01); *A61P 35/00* (2018.01); *A61P 35/02* (2018.01); *A61K 2039/505* (2013.01); *C07K 2317/24* (2013.01); *C07K 2317/52* (2013.01); *C07K 2317/565* (2013.01); *C07K 2317/732* (2013.01); *C07K 2317/734* (2013.01)

(58) Field of Classification Search
CPC ................................................. C07K 16/2896
See application file for complete search history.

(56) References Cited

U.S. PATENT DOCUMENTS

| | | |
|---|---|---|
| 2008/0112961 A1 | 5/2008 | Stavenhagen et al. |
| 2008/0138349 A1 | 6/2008 | Stavenhagen et al. |
| 2011/0250203 A1 | 10/2011 | Klitgaard et al. |
| 2013/0224190 A1 | 8/2013 | Vermot-Desroches et al. |
| 2014/0134162 A1 | 5/2014 | Stavenhagen et al. |
| 2018/0009902 A1 | 1/2018 | Stavenhagen et al. |
| 2019/0077872 A1 | 3/2019 | Igawa |
| 2020/0276326 A1* | 9/2020 | Boitano ............. A61K 47/6831 |

FOREIGN PATENT DOCUMENTS

| | | |
|---|---|---|
| WO | WO-2008121160 | 10/2008 |

OTHER PUBLICATIONS

McCarthy et al. (J. Immunol. Methods, 251(1-2): 137-149, 2001) (Year: 2001).*
Lin et al. (African Journal of Biotechnology, 10(79):18294-18302, 2011) (Year: 2011).*
European Search Report dated Sep. 2, 2020 in European Application No. 20 30 5555.

* cited by examiner

*Primary Examiner* — Elizabeth C. Kemmerer
*Assistant Examiner* — Ashley H. Gao
(74) *Attorney, Agent, or Firm* — B. Aaron Schulman, Esq.; Stites & Harbison, PLLC

(57) ABSTRACT

Novels antibodies, preferably monoclonal antibodies, or antigen-binding fragments thereof, said antibody or fragment thereof specifically binding to CD5. These antibodies may be used as a medicament, especially in the treatment of diseases in immunomodulation, inflammation, virology, infectiology, autoimmunity and oncology domains. Immune cells and/or cancer cells targeted by the invention are expressing CD5 antigen. These antibodies may be in particular chimeric or humanized. The invention also relates to pharmaceutical compositions, such as immunomodulator, anti-cancerous and anti-infectious compositions, containing such an antibody or antigen-binding fragment and methods of use of these, either for laboratory work, in drug manufacturing, such as in cell therapy cells production, or for medical treatment.

16 Claims, 15 Drawing Sheets

Specification includes a Sequence Listing.

```
<------------------------------------ H-FR1-IMGT ------------------------------------
 E   V   K   L   E   E   S   G   G   G   L   V   Q   P   G   G   S   M   K
GAG GTG AAG CTT GAG GAG TCT GGA GGG GGC TTG GTG CAA CCT GGA GGA TCC ATG AAA

------------------------------>        H-CDR1-IMGT          <----------------------
 L   S   C   V   A   S   G   F   T   F   S   N   Y   W   M   N   W   V   R
CTC TCC TGT GTT GCC TCT GGA TTC ACT TTC AGT AAC TAC TGG ATG AAC TGG GTC CGC

--------------- H-FR2-IMGT ------------------------>       H-CDR2-IMGT
 Q   S   P   E   K   G   L   E   W   V   A   E   I   R   L   K   S   N   N
CAG TCT CCA GAG AAG GGG CTT GAA TGG GTT GCT GAA ATT AGA TTG AAA TCT AAT AAT

---------   <-----------------------------------------------------------------------
 Y   A   T   H   Y   A   E   S   V   K   G   R   F   T   I   S   R   D   D
TAT GCA ACA CAT TAT GCG GAG TCT GTG AAA GGG AGG TTC ACC ATC TCA AGA GAT GAT

------------------------- H-FR3-IMGT ----------------------------------------------
 S   R   S   S   V   Y   L   Q   M   N   N   L   R   A   E   D   T   G   I
TCC AGA AGT AGT GTC TAC CTG CAA ATG AAC AAC TTA AGA GCT GAA GAC ACT GGC ATT

-------------->           H-CDR3-IMGT
 Y   Y   C   T   R   D   W   E   F   A   Y   W   G   Q   G   T   L   V   T
TAT TAC TGT ACC AGG GAC TGG GAG TTT GCT TAC TGG GGC CAA GGG ACT CTG GTC ACC

V   S   S
GTC TCC TCA
```

FIG.12

```
<------------------------- L-FR1-IMGT ---------------------------------------------
 D   I   V   L   T   Q   S   P   A   S   L   A   V   S   L   G   Q   R   A
GAC ATT GTA CTG ACC CAG TCT CCA GCC TCT TTG GCT GTG TCT CTA GGG CAG AGG GCC

-------------------------->        L-CDR1-IMGT                          <--------
 T   I   S   C   R   T   S   E   S   V   D   N   Y   G   S   S   S   M   N
ACC ATA TCC TGC AGA ACC AGT GAA AGT GTT GAT AAT TAT GGC AGT AGT TCT ATG AAC

----------------------------- L-FR2-IMGT ------------------------> L-CDR2-IMGT <---
 W   F   Q   Q   K   P   G   Q   P   P   K   L   L   I   Y   R   A   S   N
TGG TTC CAG CAG AAA CCA GGA CAG CCA CCC AAA CTC CTC ATC TAC CGT GCA TCC AAC

------------------------------------------------------------------------------------
 L   D   S   G   I   P   A   R   F   S   G   S   G   S   R   S   D   F   T
CTA GAT TCT GGG ATC CCT GCC AGG TTC AGT GGC AGT GGG TCT AGG TCA GAC TTC ACC

------------------------- L-FR3-IMGT ---------------------------->
 L   T   I   N   P   V   E   A   D   D   V   A   T   Y   Y   C   Q   Q   S
CTC ACC ATT AAT CCT GTG GAG GCT GAT GAT GTT GCA ACC TAT TAC TGT CAG CAA AGT

_____   H-CDR3-IMGT
 N   E   D   L   P   Y   T   F   G   G   G   T   K   L   E   I   K
AAC GAG GAT CTT CCG TAC ACG TTT GGA GGG GGA ACC AAG CTC GAG ATC AAA
```

FIG.13

```
<---------------------- H-FR1-IMGT ---------------------------------
  E   V   Q   L   V   E   S   G   G   G   L   V   Q   P   G   G   S
 GAA GTT CAG CTT GTT GAA AGT GGA GGT GGT TTG GTA CAG CCA GGT GGA AGC

----------------------------------->       H-CDR1-IMGT       <-----
  L   K   L   S   C   A   A   S   G   F   T   F   S   N   Y   W   M
 CTC AAA CTC AGT TGC GCC GCC TCT GGT TTT ACC TTC TCA AAC TAC TGG ATG

------------------------ H-FR2-IMGT ---------------------------------->
  H   W   V   R   Q   A   S   G   K   G   L   E   W   V   A   E   I
 CAC TGG GTT CGC CAG GCC AGC GGG AAG GGG CTT GAA TGG GTG GCA GAA ATA

H-CDR2-IMGT              <---------------------------------
  R   S   K   A   N   S   Y   A   T   A   Y   A   A   S   V   K   G
 AGG TCC AAG GCC AAC AGT TAC GCT ACA GCT TAT GCC GCT TCA GTC AAA GGT

---------------- H-FR3-IMGT ---------------------------------
  R   F   T   I   S   R   D   D   S   K   N   T   A   Y   L   Q   M
 CGG TTC ACT ATC TCC CGT GAC GAC AGT AAG AAT ACT GCT TAC CTG CAG ATG

----------------------------------------------->     H-CDR3-IMGT
  N   S   L   K   T   E   D   T   A   V   Y   Y   C   T   R   D   W
 AAT AGT CTG AAA ACA GAG GAC ACT GCC GTG TAT TAC TGC ACA CGC GAT TGG

_____
  E   F   A   Y   W   G   Q   G   T   L   V   T   V   S   S
 GAA TTC GCA TAC TGG GGG CAG GGA ACA CTG GTC ACT GTG AGT AGT
```

FIG.14

```
<---------------------- L-FR1-IMGT ---------------------------------
  D   I   V   M   T   Q   S   P   D   S   L   A   V   S   L   G   E
 GAT ATT GTC ATG ACT CAG TCA CCT GAT TCC TTG GCT GTT TCT CTC GGC GAA

----------------------------------->         L-CDR1-IMGT
  R   A   T   I   N   C   K   S   S   Q   S   V   D   N   Y   G   S
 CGA GCT ACC ATC AAC TGT AAG AGT TCC CAG AGT GTA GAC AAT TAC GGC AGC

<---------------------- L-FR2-IMGT -------------------------
  S   S   L   A   N   Y   Q   Q   K   P   G   Q   P   P   K   L   L
 TCA AGT CTC GCT TGG TAC CAG CAG AAG CCT GGG CAG CCT CCC AAA CTG TTG

---------->_L-CDR2-IMGT__ <---------------------------------
  I   Y   R   A   S   N   L   D   S   G   V   P   D   R   F   S   G
 ATA TAT AGG GCA AGT AAC CTG GAC TCC GGC GTG CCA GAC CGA TTC AGT GGT

------------------------- L-FR3-IMGT ---------------------------
  S   G   S   G   T   D   F   T   L   T   I   S   S   V   Q   A   E
 AGC GGC TCC GGT ACT GAT TTC ACC CTG ACC ATC TCC TCC GTG CAG GCT GAG

-------------------------------------->       H-CDR3-IMGT
  D   V   A   V   Y   Y   C   Q   Q   S   N   E   D   L   P   Y   T
 GAT GTG GCA GTA TAT TAC TGT CAG CAA TCT AAT GAA GAT TTG CCC TAC ACC

F   G   Q   G   T   K   L   E   I   K
 TTT GGA CAG GGC ACT AAA CTG GAG ATC AAG
```

FIG.15

```
<-------------------------------- H-FR1-IMGT ----------------------------------
 E   V   Q   L   V   E   S   G   G   G   L   V   Q   P   G   G   S   L   K
GAA GTT CAG CTT GTT GAA AGT GGA GGT GGT TTG GTA CAG CCA GGT GGA AGC CTC AAA

-------------------->          H-CDR1-IMGT          <-------------------------
 L   S   C   A   A   S   G   F   T   F   S   N   Y   W   M   N   W   V   R
CTC AGT TGC GCC GCC TCT GGT TTT ACC TTC TCA AAC TAC TGG ATG AAC TGG GTT CGC

----------------- H-FR2-IMGT ---------------------->          H-CDR2-IMGT
 Q   A   S   G   K   G   L   E   W   V   G   R   I   R   L   K   A   N   N
CAG GCC AGC GGG AAG GGG CTT GAA TGG GTG GGA AGA ATA AGG CTC AAG GCC AAC AAT

<---------------------------------------------------------------
 Y   A   T   A   Y   A   A   S   V   K   G   R   F   T   I   S   R   D   D
TAC GCT ACA GCT TAT GCC GCT TCA GTC AAA GGT CGG TTC ACT ATC TCC CGT GAC GAC

---------------------- H-FR3-IMGT --------------------------------------------
 S   K   N   T   A   Y   L   Q   M   N   S   L   K   T   E   D   T   A   V
AGT AAG AAT ACT GCT TAC CTG CAG ATG AAT AGT CTG AAA ACA GAG GAC ACT GCC GTG

-------------->          H-CDR3-IMGT
 Y   Y   C   T   R   D   W   E   F   A   Y   W   G   Q   G   T   L   V   T
TAT TAC TGC ACA CGC GAT TGG GAA TTC GCA TAC TGG GGG CAG GGA ACA CTG GTC ACT

V   S   S
GTG AGT AGT
```

FIG.16

```
CGA ACT GTG GCT GCA CCA TCT GTC TTC ATC TTC CCG CCA TCT GAT GAG CAG
 R   T   V   A   A   P   S   V   F   I   F   P   P   S   D   E   Q
TTG AAA TCT GGA ACT GCC TCT GTT GTG TGC CTG CTG AAT AAC TTC TAT CCC
 L   K   S   G   T   A   S   V   V   C   L   L   N   N   F   Y   P
AGA GAG GCC AAA GTA CAG TGG AAG GTG GAT AAC GCC CTC CAA TCG GGT AAC
 R   E   A   K   V   Q   W   K   V   D   N   A   L   Q   S   G   N
TCC CAG GAG AGT GTC ACA GAG CAG GAC AGC AAG GAC AGC ACC TAC AGC CTC
 S   Q   E   S   V   T   E   Q   D   S   K   D   S   T   Y   S   L
AGC AGC ACC CTG ACG CTG AGC AAA GCA GAC TAC GAG AAA CAC AAA GTC TAC
 S   S   T   L   T   L   S   K   A   D   Y   E   K   H   K   V   Y
GCC TGC GAA GTC ACC CAT CAG GGC CTG AGC TCG CCC GTC ACA AAG AGC TTC
 A   C   E   V   T   H   Q   G   L   S   S   P   V   T   K   S   F
AAC AGG GGA GAG TGT
 N   R   G   E   C
```

FIG.17

```
<----------------------------------------------------------------------------------
GCC TCC ACC AAG GGC CCA TCG GTC TTC CCC CTG GCA CCC TCC TCC AAG AGC ACC TCT GGG GGC
 A   S   T   K   G   P   S   V   F   P   L   A   P   S   S   K   S   T   S   G   G
------------------------------------------------------------------------------------
ACA GCG GCC CTG GGC TGC CTG GTC AAG GAC TAC TTC CCC GAA CCG GTG ACG GTG TCG TGG AAC
 T   A   A   L   G   C   L   V   K   D   Y   F   P   E   P   V   T   V   S   W   N
----------------------- CH1 -------------------------------------------------------
TCA GGC GCC CTG ACC AGC GGC GTG CAC ACC TTC CCG GCT GTC CTA CAG TCC TCA GGA CTC TAC
 S   G   A   L   T   S   G   V   H   T   F   P   A   V   L   Q   S   S   G   L   Y
------------------------------------------------------------------------------------
TCC CTC AGC AGC GTC GTG ACC GTG CCC TCC AGC AGC TTG GGC ACC CAG ACC TAC ATC TGC AAC
 S   L   S   S   V   V   T   V   P   S   S   S   L   G   T   Q   T   Y   I   C   N
------------------------------------------> <--------------------------------------
GTG AAT CAC AAG CCC AGC AAC ACC AAG GTG GAC AAG AAA GTT GAG CCC AAA TCT TGT GAC AAA
 V   N   H   K   P   S   N   T   K   V   D   K   K   V   E   P   K   S   C   D   K
- HINGE - - - - - - - - -> <-------------------------------------------------------
ACT CAC ACA TGC CCA CCG TGC CCA GCA CCT GAA CTC CTG GGG GGA CCG TCA GTC TTC CTC TTC
 T   H   T   C   P   P   C   P   A   P   E   L   L   G   G   P   S   V   F   L   F
------------------------------------------------------------------------------------
CCC CCA AAA CCC AAG GAC ACC CTC ATG ATC TCC CGG ACC CCT GAG GTC ACA TGC GTG GTG GTG
 P   P   K   P   K   D   T   L   M   I   S   R   T   P   E   V   T   C   V   V   V
------------------------------------------------------------------------------------
GAC GTG AGC CAC GAA GAC CCT GAG GTC AAG TTC AAC TGG TAC GTG GAC GGC GTG GAG GTG CAT
 D   V   S   H   E   D   P   E   V   K   F   N   W   Y   V   D   G   V   E   V   H
----------------------- CH2 -------------------------------------------------------
AAT GCC AAG ACA AAG CCG CGG GAG GAG CAG TAC AAC AGC ACG TAC CGT GTG GTC AGC GTC CTC
 N   A   K   T   K   P   R   E   E   Q   Y   N   S   T   Y   R   V   V   S   V   L
------------------------------------------------------------------------------------
ACC GTC CTG CAC CAG GAC TGG CTG AAT GGC AAG GAG TAC AAG TGC AAG GTC TCC AAC AAA GCC
 T   V   L   H   Q   D   W   L   N   G   K   E   Y   K   C   K   V   S   N   K   A
------------------------------------------> <--------------------------------------
CTC CCA GCC CCC ATC GAG AAA ACC ATC TCC AAA GCC AAA GGG CAG CCC CGA GAA CCA CAG GTG
 L   P   A   P   I   E   K   T   I   S   K   A   K   G   Q   P   R   E   P   Q   V
------------------------------------------------------------------------------------
TAC ACC CTG CCC CCA TCC CGG GAT GAG CTG ACC AAG AAC CAG GTC AGC CTG ACC TGC CTG GTC
 Y   T   L   P   P   S   R   D   E   L   T   K   N   Q   V   S   L   T   C   L   V
- - - - - - - - - - - - CH3 - - - - - - - - - - - - - - - - - - - - - - - - - - - -
AAA GGC TTC TAT CCC AGC GAC ATC GCC GTG GAG TGG GAG AGC AAT GGG CAG CCG GAG AAC AAC
 K   G   F   Y   P   S   D   I   A   V   E   W   E   S   N   G   Q   P   E   N   N
------------------------------------------------------------------------------------
TAC AAG ACC ACG CCT CCC GTG CTG GAC TCC GAC GGC TCC TTC TTC CTC TAC AGC AAG CTC ACC
 Y   K   T   T   P   P   V   L   D   S   D   G   S   F   F   L   Y   S   K   L   T
------------------------------------------------------------------------------------
GTG GAC AAG AGC AGG TGG CAG CAG GGG AAC GTC TTC TCA TGC TCC GTG ATG CAT GAG GCT CTG
 V   D   K   S   R   W   Q   Q   G   N   V   F   S   C   S   V   M   H   E   A   L
------------------------------------------------------------------------------------
CAC AAC CAC TAC ACG CAG AAG AGC CTC TCC CTG TCT CCG GGT AAA
 H   N   H   Y   T   Q   K   S   L   S   L   S   P   G   K
```

FIG.18

SEQ ID NO: 33
GCCTCCACCAAGGGCCCATCGGTCTTCCCCCTGGCACCCTCCTCCAAGAGCACCTCTGGGGGCACAGCGGCCCTGGGCTGCCTGG
TCAAGGACTACTTCCCCGAACCGGTGACGGTGTCGTGGAACTCAGGCGCCCTGACCAGCGGCGTGCACACCTTCCCGGCTGTCCT
ACAGTCCTCAGGACTCTACTCCCTCAGCAGCGTCGTGACCGTGCCCTCCAGCAGCTTGGGCACCCAGACCTACATCTGCAACGTG
AATCACAAGCCCAGCAACACCAAGGTGGACAAGAAAGTTGAGCCCAAATCTTGTGACAAAACTCACACATGCCCACCGTGCCCAG
CACCTGAACTCCTGGGGGGACCGTCAGTCTTCCTCTTACCCCAAAACCCAAGGACACCCTCATGATCTCCCGGACCCCTGAGGT
CACATGCGTGGTGGTGGACGTGAGCCACGAAGACCCTGAGGTCAAGTTCAACTGGTACGTGGACGGCGTGGAGGTGCATAATGCC
AAGACAAAGCCGCGGGAGGAGCAGTACAACAGCACGCTCCGTGTGGTCAGCCTCCTCACCGTCCTGCACCAGGACTGGCTGAATG
GCAAGGAGTACAAGTGCAAGGTCTCCAACGCAGCCCTCCCAGCCCCCATCGCGAAAACCATCTCCAAAGCCAAAGGGCAGCCCCG
AGAACCACAGGTGTACACCCTGCCCCCATCCCGGGATGAGCTGACCAAGAACCAGGTCAGCCTGACCTGCCTGGTCAAAGGCTTC
TATCCCAGCGACATCGCCGTGGAGTGGGAGAGCAATGGGCAGCCGGAGAACAACTACAAGACCACGCCTCCGTGCTGGACTCCG
ACGGCTCCTTCTTCCTCTACAGCAAGCTCACCGTGGACAAGAGCAGGTGGCAGCAGGGGAACGTCTTCTCATGCTCCGTGATGCA
TGAGGCTCTGCACAACCACTACACGCAGAAGAGCCTCTCCCTGTCTCCGGGTAAA

SEQ ID NO: 32

ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLLPPKPKDTLMISRTPEVTCVVVDVSHE
DPEVKFNWYVDGVEVHNAKTKPPEEQYNSTLRVVSLLTVLHQDWLNGKEYKCKVSNAALPAPIAKTISKAKGQPRE
PQVYTLPPSRDELTKNQVSLTCLVKGFYPSDIAVEWESNGQPENNYKTTPLVLDSDGSFFLYSKLTVDKSRWQQGN
VFSCSVMHEALHNHYTQKSLSLSPGK

FIG.19

SEQ ID NO: 35
GCCTCCACCAAGGGCCCATCGGTCTTCCCCCTGGCACCCTCCTCCAAGAGCACCTCTGGGGGCACAGCGGCCCTGGGCTGCCTGG
TCAAGGACTACTTCCCCGAACCGGTGACGGTGTCGTGGAACTCAGGCGCCCTGACCAGCGGCGTGCACACCTTCCCGGCTGTCCT
ACAGTCCTCAGGACTCTACTCCCTCAGCAGCGTCGTGACCGTGCCCTCCAGCAGCTTGGGCACCCAGACCTACATCTGCAACGTG
AATCACAAGCCCAGCAACACCAAGGTGGACAAGAAAGTTGAGCCCAAATCTTGTGACAAAACTCACACATGCCCACCGTGCCCAG
CACCTGAACTCCTGGGGGGACCGTCAGTCTTCCTCTTACCCCAAAACCCAAGGACACCCTCATGATCTCCCGGACCCCTGAGGT
CACATGCGTGGTGGTGGACGTGAGCCACGAAGACCCTGAGGTCAAGTTCAACTGGTACGTGGACGGCGTGGAGGTGCATAATGCC
AAGACAAAGCCGCGGGAGGAGCAGTACAACAGCACGCTCCGTGTGGTCAGCCTCCTCACCGTCCTGCACCAGGACTGGCTGAATG
GCAAGGAGTACAAGTGCAAGGTCTCCAACGCAGCCCTCCCAGCCCCCATCGAGAAAACCATCTCCAAAGCCAAAGGGCAGCCCCG
AGAACCACAGGTGTACACCCTGCCCCCATCCCGGGATGAGCTGACCAAGAACCAGGTCAGCCTGACCTGCCTGGTCAAAGGCTTC
TATCCCAGCGACATCGCCGTGGAGTGGGAGAGCAATGGGCAGCCGGAGAACAACTACAAGACCACGCCTCCGTGCTGGACTCCG
ACGGCTCCTTCTTCCTCTACAGCAAGCTCACCGTGGACAAGAGCAGGTGGCAGCAGGGGAACGTCTTCTCATGCTCCGTGATGCA
TGAGGCTCTGCACAACCACTACACGCAGAAGAGCCTCTCCCTGTCTCCGGGTAAA

SEQ ID NO: 34

ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLLPPKPKDTLMISRTPEVTCVVVDVSHE
DPEVKFNWYVDGVEVHNAKTKPPEEQYNSTLRVVSLLTVLHQDWLNGKEYKCKVSNAALPAPIEKTISKAKGQPRE
PQVYTLPPSRDELTKNQVSLTCLVKGFYPSDIAVEWESNGQPENNYKTTPLVLDSDGSFFLYSKLTVDKSRWQQGN
VFSCSVMHEALHNHYTQKSLSLSPGK

FIG.20

SEQ ID NO: 37

GCCTCCACCAAGGGCCCATCGGTCTTCCCCCTGGCACCCTCCTCCAAGAGCACCTCTGGGGGCACAGCGGCCCTGGGCTGCCTGG
TCAAGGACTACTTCCCCGAACCGGTGACGGTGTCGTGGAACTCAGGCGCCCTGACCAGCGGCGTGCACACCTTCCCGGCTGTCCT
ACAGTCCTCAGGACTCTACTCCCTCAGCAGCGTCGTGACCGTGCCCTCCAGCAGCTTGGGCACCCAGACCTACATCTGCAACGTG
AATCACAAGCCCAGCAACACCAAGGTGGACAAGAAAGTTGAGCCCAAATCTTGTGACAAAACTCACACATGCCCACCGTGCCCAG
CACCTGAACTCCTGGGGGGACCGTCAGTCTTCCTCTTCCCCCAAAACCCAAGGACACCCTCATGATCTCCCGGACCCCTGAGGT
CACATGCGTGGTGGTGGACGTGAGCCACGAAGACCCTGAGGTCAAGTTCAACTGGTACGTGGACGGCGTGGAGGTGCATAATGCC
AAGACAAAGCCGCGGGAGGAGCAGTACAACAGCACGCTCCGTGTGGTCAGCATCCTCACCGTCCTGCACCAGGACTGGCTGAATG
GCAAGGAGTACAAGTGCAAGGTCTCCAACGCAGCCCTCCCAGCCCCCATCGAGAAAACCATCTCCAAAGCCAAAGGGCAGCCCCG
AGAACCACAGGTGTACACCCTGCCCCCATCCCGGGATGAGCTGACCAAGAACCAGGTCAGCCTGACCTGCCTGGTCAAAGGCTTC
TATCCCAGCGACATCGCCGTGGAGTGGGAGAGCAATGGGCAGCCGGAGAACAACTACAAGACCACGCCTCCCGTGCTGGACTCCG
ACGGCTCCTTCTTCCTCTACAGCAAGCTCACCGTGGACAAGAGCAGGTGGCAGCAGGGGAACGTCTTCTCATGCTCCGTGATGCA
TGAGGCTCTGCACAACCACTACACGCAGAAGAGCCTCTCCCTGTCTCCGGGTAAA

SEQ ID NO: 36

ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLLPPKPKDTLMISRTPEVTCVVVDVSHE
DPEVKFNWYVDGVEVHNAKTKPPEEQYNSTLRVVSILTVLHQDWLNGKEYKCKVSNAALPAPIEKTISKAKGQPRE
PQVYTLPPSRDELTKNQVSLTCLVKGFYPSDIAVEWESNGQPENNYKTTPLVLDSDGSFFLYSKLTVDKSRWQQGN
VFSCSVMHEALHNHYTQKSLSLSPGK

FIG.21

ANTI-CD5 ANTIBODIES AND METHODS OF USE THEREOF

FIELD OF THE INVENTION

The present invention relates to the fields of immunology, and more specifically, to antibodies or antibody fragment (i.e. antigen-binding fragment) thereof, specifically binding CD5, that can be used in the treatment of diseases, more precisely in immunomodulation, inflammation, virology, infectiology, autoimmunity and oncology domains. Immune cells and/or cancer cells targeted by the invention are expressing CD5 antigen. These antibodies may be in particular chimeric or humanized. The invention also relates to pharmaceutical compositions, such as immunomodulator, anti-cancerous and anti-infectious compositions, containing an antibody or antigen-binding fragment according to this invention and methods of use of these, either for laboratory work, in drug manufacturing, such as in cell therapy cells production, or for medical treatment.

BACKGROUND OF THE INVENTION

CD5 is a type I glycoprotein and a member of the scavenger-receptor family expressed with the antigen-specific receptors on T and B-1a lymphocytes. CD5 is characterized by a broader biology that includes its role as regulator of cell death and as a receptor for pathogen associated molecular patterns, in addition to its previously described function as an inhibitory receptor (G. Soldevilla, *Cur Opinion Immunol* 2011). These identified properties make this receptor a potential candidate to be targeted for therapeutic intervention in leukemia and effector cells to exogeneous (infectious) or endogenous (autoimmune, tumoral) antigens as well as immune modulation.

More precisely, CD5 is expressed by thymocytes, mature T-cells and a subset of mature B-cells. CD5 is associated both physically and functionally with the TCR/CD3 complex and with the B-cell receptor (BCR). CD5 negatively regulates Ag receptor-mediated signaling. CD5 thus plays an important role as a physiological regulator of T-cell immune responses, in the maintenance of immune homeostasis and in immune tolerance. The CD5 antigen is expressed on different types of immune cells as T effector conventional cells (CD4+CD3+Foxp3−) or T regulatory cells (CD4+CD3+Foxp3+).

CD5 is involved in modulation of lymphocyte activation and in the differentiation process. CD5 itself, CD5L, CD72, gp80-40 and Ig framework structures are purposed ligands for CD5. The exact role of CD5-ligand(s) interactions remains to be clarified. CD5 is associated with CD79a and CD79b transduction partner of surface IgM in the vicinity of B cell receptor (BCR). CD79a and CD79b are phosphorylated by the Lyn and other tyrosine kinases such as Syk, Zap70, as well as the tyrosine phosphatase SHP1.

Currently, a great deal of attention has focused on the development of novel immunotherapy strategies for the treatment of inflammation, virology, autoimmunity and oncology.

The increasing availability of different monoclonal antibodies (MAbs) opens the way to more specific biologic therapy of cancer patients. Rituximab has very limited effect in CLL compared to the results in other indolent B-cell lymphomas/leukemia. The anti-CD52 MAb Campath-1H has proven some efficacy but the profound immunodeficiency associated with Campath-1H limits its use. Current strategies for improving the results in CLL and in Mantle Cell Lymphoma (MCL) focus on MAb chemotherapy combinations and the development of MAbs targeting other antigens than CD20 and CD52.

CD5 is expressed on CLL and on B-cell MCL. Both diseases are incurable with conventional chemotherapy. Cross-linking of CD5 with antibody can induce apoptosis in Chronic Lymphocytic Leukemia (CLL).

CD5 is rapidly emerging as an important regulator of T-cell and B-1a cell survival. This discovery explains why loss of regulation in T-cells and B-1a cells in CD5−/−mice does not lead to autoimmunity (Axtell R. C, *J. Immunol* 2004). Moreover, it has been shown that CD5 expression levels on human tumor antigen specific CD8 CTL inversely correlated with susceptibility to autologous tumor-mediated activation induced cell death (AICD). CD5 promoted survival of CTL by down-regulating FasL and leading to inhibition of caspase 8 activity. Tumor-infiltrating lymphocytes (TILs) with lower expression of CD5 exhibited the greatest anti-tumor activity (G. Dorothee, *J. Immunol.,* 2005). Moreover CD5 downmodulation induced with IL-7 and IL-21 leads to increased responsiveness of CD8 T cells to antigen and provides a mechanism by which CTLs can develop adaptive ability to increase their antitumor activity (J. Gagnon, *Immunol Cell Biol,* 2010). Similarly, CD5 up-regulation has been shown to protect autoreactive CD4 T cells from Fas-mediated death (K. P. Ryan, *J Leuk Biol,* 2005).

In CD5 expressing B cells, survival is associated with CD5-dependent IL-10 production (H. Gary-Gouy, *Blood,* 2002). CD5 provides viability signals to B cell chronic lymphocyte leukemia (B-CLL) by a mechanism that involves PKC (G. Perez-Chacon, *Leuk Res* 2007).

It has been also reported that CD5 is a molecule important for Hepatitis C virus (HCV) entry into human T lymphocytes. Hepatitis C virus (HCV) is one of the main causes of chronic liver disease (M. Sarhan, *Journal of Virology,* 2012). Although infection of hepatocytes is mainly responsible for manifestations of hepatitis C, the virus also invades the immune system. This finding provides direct insight into the mechanism of HCV lymphotropism and defines a target for potential interventions against HCV propagating in this extrahepatic compartment. Blocking of T cell CD5 with antibody or silencing with specific short hairpin RNA (shRNA) could decreased cell susceptibility to HCV.

Recognition of pathogen-associated molecular patterns (PAMPs) by pathogen recognition receptors (PRRs) on immune associated cells is critical for host defense against pathogens. It has been hypothesized that recognition of PAMPs by these lymphoid scavenger receptors, particularly CD5, may result in the optimization of anti-infectious responses while minimizing the activation of auto reactive cell clones (L. L. Jenz *Proc Natl Acad Sci* 2009). The CD5 binding by microbial components would allow the preferential activation of those lymphocytes with the highest reactive TCR or BRC, able to overcome the negative signals of CD5 (L. L. Lenz, *Proc Nath Acad Sci,* 2009).

There is thus a need for efficient antibodies that may be used alone or in combination with other therapeutic molecule (including antibody) in the depletion of cancer cells and in immunotherapy strategies for the treatment of inflammation, virology, infectiology, autoimmunity and oncology, for example for treating human immune system and malignancies harboring CD5. The CD5 antigen is also an attractive target for antibody-based active and passive immunotherapy.

SUMMARY OF INVENTION

The present invention thus relates to antibodies specifically binding to CD5. Such antibodies may be full-size monoclonal antibodies specifically binding to CD5, or CD5-binding fragments thereof. A murine monoclonal antibody called mR007 has been selected which binds to CD5 and exhibits interesting and properties rendering it a good basis for developing chimeric and humanized antibodies for therapeutic use. From this murine antibody, the applicant indeed derived and produced antigen (CD5)-binding molecules that keep or substantially keep the specific set of CDRs of the murine antibody and/or the same or substantially same binding ability, especially antibodies that are more suited to the treatment of a given mammal species, especially a human. In particular, powerful chimeric and humanized monoclonal antibodies were generated, having the same set of CDRs than the murine, or having a variant set of CDRs, and/or having a human IgG1 Fc region or optimized/variant forms. This allows the person skilled in the art, based on the following description and its general knowledge to prepare antibodies "derived from" these murine and humanized monoclonal antibody, and antigen-binding fragments thereof. As it will be apparent from the following, the terms "derived from" may encompass different CD5-binding molecules retaining or substantially retaining the antigen-binding properties of the parental monoclonal antibody.

The antibodies according to the invention comprise CDR sequences, or VH and VL sequences comprising CDR sequences. The CDR sequences may be defined in accordance with IMGT, Kabat, or the Common numbering system (CNS, which retain the common sequence between IMGT and Kabat). An object of the invention is thus an anti-CD5 monoclonal antibody or a CD5-binding fragment thereof, such as a murine (e.g. mR007), a chimeric or a humanized monoclonal antibody, or an antigen-binding fragment thereof, comprising L-CDR 1, 2 and 3 and/or H-CDR 1, 2 and 3 as follows (Table 1):

|  | SEQ ID No: IMGT | SEQ ID No: Kabat | SEQ Common ID numbering No: system |
|---|---|---|---|
| VL | | | |
| L-CDR1 | 1 ESVDNYGSSS | 6 RTSESVDNYGSSSMN | 1 ESVDNYGSSS |
| L-CDR2 | RAS | 7 RASNLDS | RAS |
| L-CDR3 | 2 QQSNEDLPYT | 2 QQSNEDLPYT | 2 QQSNEDLPYT |
| VH | | | |
| H-CDR1 | 3 GFTFSNYW | 8 NYWMN | 11 SNYW |
| H-CDR2 | 4 IRLKSNNYAT | 9 EIRLKSNNYATHYAESVKG | 4 IRLKSNNYAT |
| H-CDR3 | 5 TRDWEFAY | 10 DWEFAY | 10 DWEFAY |

The antibodies and antigen-binding fragments of the invention may thus be, in particular, any antibodies, monoclonal antibodies, chimeric antibodies, humanized antibodies, or any antigen-binding fragment of them, comprising the sets of 3 H-CDRs and 3 L-CDRs of Table 1.

A "humanized antibody" or "chimeric antibody" shall mean an antibody derived from the parent murine antibody by the methods available to the skilled person and for example, those disclosed herein. Preferably, a "humanized antibody" or "chimeric antibody", or an antigen-binding fragment thereof, will comprise the set of 6 CDRs of the murine antibody mR007.

All these antibodies, such as in particular the humanized or chimeric antibodies, and the antigen-binding fragments, retain or substantially retain the antigen-binding properties of the parental murine antibody mR007. The disclosure of the VH and VL sequences and set of CDRs of the parental murine antibody is also deemed allowing the skilled person developing full human antibodies and bispecific antibodies.

The CDRs or some of them may differ from the murine CDRs following SDR approaches (super-grafting) or other useful methods. Is also encompassed variant humanized antibodies wherein up to 1, 2, 3, 4, 4, 5, 6, 7, 8, 9, 10 amino acids have been changed in the 6 CDRs as disclosed in Table 1, especially based on the Kabat numbering, wherein the variant humanized antibody retain or substantially retain the antigen-binding properties of the parental murine antibody mR007 or the humanized antibody comprising the 6 CDRs of Table 1.

The present invention thus discloses variant L-CDR1 and H-CDR2 (see Tables 2 and 3), and these variants are those present in the herein disclosed humanized monoclonal antibodies 7Hz116 and 7Hz118 or binding fragments thereof.

An object of the invention is thus an anti-CD5 monoclonal antibody, preferably humanized, such as 7Hz116, or a CD5-binding fragment thereof, comprising L-CDR 1, 2 and 3 and/or H-CDR 1, 2 and 3 as follows (Table 2):

|  | SEQ ID No: IMGT | SEQ ID No: Kabat | SEQ Common ID numbering No: system |
|---|---|---|---|
| VL | | | |
| L-CDR1 | 12 QSVDNYGSSS | 14 KSSQSVDNYGSSSLA | 12 QSVDNYGSSS |
| L-CDR2 | RAS | 7 RASNLDS | RAS |
| L-CDR3 | 2 QQSNEDLPYT | 2 QQSNEDLPYT | 2 QQSNEDLPYT |
| VH | | | |
| H-CDR1 | 3 GFTFSNYW | 8 NYWMN | 11 SNYW |
| H-CDR2 | 13 IRSKANSYAT | 15 EIRSKANSYATAYAASVKG | 13 IRSKANSYAT |
| H-CDR3 | 5 TRDWEFAY | 10 D WE FAY | 10 DWEFAY |

Another object of the invention is thus an anti-CD5 monoclonal antibody, preferably humanized, such as 7Hz118, or a CD5-binding fragment thereof, comprising L-CDR 1, 2 and 3 and/or H-CDR 1, 2 and 3 as follows (Table 3):

|  | SEQ ID No: IMGT | SEQ ID No: Kabat | SEQ Common ID numbering No: system |
|---|---|---|---|
| VL | | | |
| L-CDR1 | 12 QSVDNYGSSS | 14 KSSQSVDNYGSSSLA | 12 QSVDNYGSSS |
| L-CDR2 | RAS | 7 RASNLDS | RAS |
| L-CDR3 | 2 QQSNEDLPYT | 2 QQSNEDLPYT | 2 QQSNEDLPYT |
| VH | | | |
| H-CDR1 | 3 GFTFSNYW | 8 NYWMN | 11 SNYW |
| H-CDR2 | 16 IRLKANNYAT | 17 RIRLKANNYATAYAASVKG | 16 IRLKANNYAT |
| H-CDR3 | 5 TRDWEFAY | 10 DWEFAY | 10 DWEFAY |

DETAILED DESCRIPTION

Antibodies

The invention thus primarily concerns an antibody, preferably monoclonal antibody, or an antigen-binding fragment thereof, said antibody or fragment thereof specifically binding to CD5 and comprising (based on Table 1)
(1) a VL chain comprising the following three CDRs: a L-CDR1 of sequence SEQ ID NO: 1, a L-CDR2 of sequence RAS, a L-CDR3 of sequence SEQ ID NO: 2; and a VH chain comprising the following three CDRs: a H-CDR1 of sequence SEQ ID NO: 3, a H-CDR2 of sequence SEQ ID NO: 4, a H-CDR3 of sequence SEQ ID NO: 5;
(2) a VL chain comprising the following three CDRs: a L-CDR1 of sequence SEQ ID NO: 6, a L-CDR2 of sequence SEQ ID NO: 7, a L-CDR3 of sequence SEQ ID NO: 2; and a VH chain comprising the following three CDRs: a H-CDR1 of sequence SEQ ID NO: 8, a H-CDR2 of sequence SEQ ID NO: 9, a H-CDR3 of sequence SEQ ID NO: 10;
(3) a VL chain comprising the following three CDRs: a L-CDR1 of sequence SEQ ID NO: 1, a L-CDR2 of sequence RAS, a L-CDR3 of sequence SEQ ID NO: 2; and a VH chain comprising the following three CDRs: a H-CDR1 of sequence SEQ ID NO: 11, a H-CDR2 of sequence SEQ ID NO: 4, a H-CDR3 of sequence SEQ ID NO: 10. More particularly, this antibody or fragment is for use as a medicament.

The invention particularly concerns an antibody, preferably monoclonal antibody, or antigen-binding fragment thereof, said antibody or fragment thereof specifically binding to CD5 and comprising a VL region of sequence SEQ ID NO: 18; a VH region of sequence SEQ ID NO: 20; or preferably a VL region of sequence SEQ ID NO: 18 and a VH region of sequence SEQ ID NO: 20. These regions are those of the murine antibody R007, and these regions comprise the sets of CDRs disclosed in Table 1 and in paragraphs (1), (2) and (3) above.

These antibodies, preferably monoclonal antibodies, according to the invention may be chimeric antibodies. In particular, they comprise a human Fc region, preferably an IgG1 human Fc region, linked to the VH region as disclosed herein (to form the Heavy Chain) and/or (preferably and) a human Kappa region, linked to the VL region as disclosed herein (to form the Light Chain). In an embodiment, the Fc region is the native Fc, especially the native human IgG1 Fc, which means that the Fc region does not comprise substitutions of one or more Fc amino acid. In an embodiment, the antibody comprises a human IgG1 Fc region or a variant human IgG1 Fc region as described hereinafter.

Thus, an object of the invention is an antibody, preferably monoclonal antibody, comprising a Heavy Chain comprising a VH chain according to paragraphs (1), (2) or (3) above, and a human Fc region, preferably an IgG1 human Fc region; and a Light Chain comprising a VL chain according to paragraphs (1), (2) or (3) above. In an embodiment, the Light Chain comprises a human Kappa region. In an embodiment, the human IgG1 Fc region is a variant human IgG1 Fc region as described hereinafter.

These monoclonal antibodies comprising a Heavy Chain comprising a VH chain according to paragraphs (1), (2) or (3) above, and a Light Chain comprising a VL chain according to paragraphs (1), (2) or (3) above, may also be humanized. Humanization is described herein after.

As described herein, the applicant generated some CDR variants with respect to the CDRs of the murine antibody mR007, which CDRs are disclosed in Table 1. These variant CDR variants prove to be efficient in the herein-disclosed humanized antibodies 7Hz116 and 7Hz118.

The invention thus also concerns an antibody, preferably monoclonal antibody, or an antigen-binding fragment thereof, said antibody or fragment thereof specifically binding to CD5 and comprising (based on Table 2)
(1a) a VL chain comprising the following three CDRs: a L-CDR1 of sequence SEQ ID NO: 12, a L-CDR2 of sequence RAS, a L-CDR3 of sequence SEQ ID NO: 2; and a VH chain comprising the following three CDRs: a H-CDR1 of sequence SEQ ID NO: 3, a H-CDR2 of sequence SEQ ID NO: 13, a H-CDR3 of sequence SEQ ID NO: 5;
(2a) a VL chain comprising the following three CDRs: a L-CDR1 of sequence SEQ ID NO: 14, a L-CDR2 of sequence SEQ ID NO: 7, a L-CDR3 of sequence SEQ ID NO: 2; and a VH chain comprising the following three CDRs: a H-CDR1 of sequence SEQ ID NO: 8, a H-CDR2 of sequence SEQ ID NO: 15, a H-CDR3 of sequence SEQ ID NO: 10;
(3a) a VL chain comprising the following three CDRs: a L-CDR1 of sequence SEQ ID NO: 12, a L-CDR2 of sequence RAS, a L-CDR3 of sequence SEQ ID NO: 2; and a VH chain comprising the following three CDRs: a H-CDR1 of sequence SEQ ID NO: 11, a H-CDR2 of sequence SEQ ID NO: 13, a H-CDR3 of sequence SEQ ID NO: 10.

The invention thus also concerns an antibody, preferably monoclonal antibody, or an antigen-binding fragment thereof, said antibody or fragment thereof specifically binding to CD5 and comprising (based on Table 3)
(1b) VL chain comprising the following three CDRs: a L-CDR1 of sequence SEQ ID NO: 12, a L-CDR2 of sequence RAS, a L-CDR3 of sequence SEQ ID NO: 2; and a VH chain comprising the following three CDRs: a H-CDR1 of sequence SEQ ID NO: 3, a H-CDR2 of sequence SEQ ID NO: 16, a H-CDR3 of sequence SEQ ID NO: 5;
(2b) a VL chain comprising the following three CDRs: a L-CDR1 of sequence SEQ ID NO: 14, a L-CDR2 of sequence SEQ ID NO: 7, a L-CDR3 of sequence SEQ ID NO: 2; and a VH chain comprising the following three CDRs: a H-CDR1 of sequence SEQ ID NO: 8, a H-CDR2 of sequence SEQ ID NO: 17, a H-CDR3 of sequence SEQ ID NO: 10;
(3b) a VL chain comprising the following three CDRs: a L-CDR1 of sequence SEQ ID NO: 12, a L-CDR2 of sequence RAS, a L-CDR3 of sequence SEQ ID NO: 2; and a VH chain comprising the following three CDRs: a H-CDR1 of sequence SEQ ID NO: 11, a H-CDR2 of sequence SEQ ID NO: 16, a H-CDR3 of sequence SEQ ID NO: 10.

In an embodiment, the antibody, preferably monoclonal antibody, according to the invention comprises a Heavy Chain comprising a VH chain according to paragraphs (1a), (2a) or (3a) above, and a human Fc region, preferably an IgG1 human Fc region; and/or (preferably and) a Light Chain comprising a VL chain according to paragraphs (1a), (2a) or (3a) above. In an embodiment, the Light Chain comprises a human Kappa region. The antibody may comprise a human IgG1 Fc region or a variant human IgG1 Fc region as described hereinafter.

In an embodiment, the antibody, preferably monoclonal antibody, according to the invention comprises a Heavy Chain comprising a VH chain according to paragraphs (1b), (2b) or (3b) above, and a human Fc region, preferably an IgG1 human Fc region; and/or (preferably and) a Light Chain comprising a VL chain according to paragraphs (1b), (2b) or (3b) above. In an embodiment, the Light Chain comprises a human Kappa region. The antibody may comprise a human IgG1 Fc region or a variant human IgG1 Fc region as described hereinafter.

In an embodiment, the antibody, preferably monoclonal antibody, according to the invention comprises a Heavy Chain comprising a VH chain according to paragraphs (1a), (2a) or (3a) above, and a Light Chain comprising a VL chain according to paragraphs (1a), (2a) or (3a) above, is humanized. The antibody may comprise a human IgG1 Fc region or a variant human IgG1 Fc region as described hereinafter.

In an embodiment, the antibody, preferably monoclonal antibody, according to the invention comprises a Heavy Chain comprising a VH chain according to paragraphs (1b), (2b) or (3b) above, and a Light Chain comprising a VL chain according to paragraphs (1b), (2b) or (3b) above; is humanized. The antibody may comprise a human IgG1 Fc region or a variant human IgG1 Fc region as described hereinafter.

The invention particularly concerns a humanized monoclonal antibody, or an antigen-binding fragment thereof, which antibody or fragment thereof comprises a humanized VL region of sequence SEQ ID NO: 22 and a humanized VH region of sequence SEQ ID NO: 24 or 26. The antibody or fragment thereof specifically binds to CD5. The antibody may comprise a human IgG1 Fc region or a variant human IgG1 Fc region as described hereinafter.

The invention particularly concerns a humanized monoclonal antibody, or an antigen-binding fragment thereof, which antibody or fragment thereof comprises a humanized Light Chain of sequence SEQ ID NO: 28 and a humanized Heavy Chain of sequence SEQ ID NO: 30 or 32. The antibody or fragment thereof specifically binds to CD5. The antibody may comprise a human IgG1 Fc region or a variant human IgG1 Fc region as described hereinafter.

The invention further concerns a humanized monoclonal antibody, or an antigen-binding fragment thereof, which antibody or fragment thereof comprises:
 (i) a Heavy Chain comprising a VH region of sequence SEQ ID NO: 24 and a human Fc region, preferably an IgG1 human Fc region; and a Light Chain comprising a VL region of sequence SEQ ID NO: 22 and a human Kappa region;
 (ii) a Heavy Chain of sequence SEQ ID NO: 30; and a Light Chain of sequence SEQ ID NO: 28;
 (iii) a Heavy Chain comprising a VH region of sequence SEQ ID NO: 24 and a human Fc region, preferably an IgG1 human Fc region; and a Light Chain comprising a VL region of sequence SEQ ID NO: 22.

The antibody or fragment thereof specifically binds to CD5. The antibody may comprise a human IgG1 Fc region or a variant human IgG1 Fc region as described hereinafter.

The invention further concerns a humanized monoclonal antibody, or an antigen-binding fragment thereof, which antibody or fragment thereof comprises:
 (i) a Heavy Chain comprising a VH region of sequence SEQ ID NO: 26 and a human Fc region, preferably an IgG1 human Fc region; and a Light Chain comprising a VL region of sequence SEQ ID NO: 22 and a human Kappa region;
 (ii) a Heavy Chain of sequence SEQ ID NO: 32; and a Light Chain of sequence SEQ ID NO: 28;
 (iii) a Heavy Chain comprising a VH region of sequence SEQ ID NO: 26 and a human Fc region, preferably an IgG1 human Fc region; and a Light Chain comprising a VL region of sequence SEQ ID NO: 22.

The antibody or fragment thereof specifically binds to CD5. The antibody may comprise a human IgG1 Fc region or a variant human IgG1 Fc region as described hereinafter.

The VH and VL regions in the monoclonal antibodies of the invention may comprise the sets of respective three H-CDRs and L-CDRs as disclosed in Tables 1, 2 and 3, and Framework Regions FR1, FR2, FR3 and FR4. In some embodiments, the Framework Regions may be those of mR007 as represented on FIGS. 10 and 11, those of 7Hz116 humanized antibody, as represented on FIGS. 12 and 13, or those of 7Hz118 humanized antibody, as represented on FIGS. 14 and 13.

The antibodies of the invention may encompass an antibody, preferably monoclonal antibody, or an antigen-binding fragment thereof, said antibody or fragment thereof specifically binding to CD5 and comprising a VH region comprising a sequence with 85, 90, 95, 96, 97, 98, 99 or 100% identity after optimal alignment with sequence SEQ ID NO: 120 24 or 26 and a VL region comprising a sequence with 85, 90, 95, 96, 97, 98, 99 or 100% identity after optimal alignment with sequence SEQ ID NO: 18 or 22.

In particular, there can be changes of some amino acids in the Framework Regions (FR) and these changes are made so as the antigen-binding properties are not changed or substantially changed. Thus, the invention also encompasses an antibody, preferably monoclonal antibody, or an antigen-binding fragment thereof, said antibody or fragment thereof specifically binding to CD5 and comprising
 a VH region comprising the H-CDR1, H-CDR2 and H-CDR3 according to IMGT, Kabat, or CNS (Table 1, 2 or 3) and Framework Regions FR1, FR2, FR3 and FR4 wherein at least one of the Framework Regions FR1, FR2, FR2 and FR4 thereof has a sequence with at least 85%, 90%, 95%, 96%, 97%, 98% or 99% of identity after optimal alignment with the respective FR1, FR2, FR3 and FR4 sequence of FIG. 8, 12, and
 a VL region comprising the L-CDR1, L-CDR2 and L-CDR3 according to IMGT, Kabat, or CNS (Table 1, 2 or 3) and Framework Regions FR1, FR2, FR3 and FR4 wherein at least one of the Framework Regions FR1, FR2, FR2 and FR4 thereof has a sequence with at least 85%, 90%, 95% 96%, 97%, 98% or 99% of identity after optimal alignment with the respective FR1, FR2, FR3 and FR4 sequence of FIG. 9 or 13.

In an embodiment, the antibody comprises a human IgG, especially human IgG1 Fc region. Based on this disclosure, the skilled person is able to modify an antibody according to the invention to comprise a variant human optimized IgG Fc region, preferably IgG1 Fc region, wherein this variant region comprises one or more amino acid substitutions, so as for example to modulate PDC, ADCC, ADPC, CDC, antibody multivalence or to attach linker, cytotoxic payload, radioactive, fluorescence probes.

The antibodies of the invention (especially chimeric and humanized) may comprise a variant Fc selected from Table 4.

TABLE 4

List of Fc variants
Name of Fc region: list of amino acids
modification with respect to native human
IgG1 Fc (called Fc0) of SEQ ID NO: 28

Fc2: E333A/D356E/L358M/A431G
Fc2bis: E333A/D356E/L358M
Fc5: A141V/P227L/E333A
Fc6: E333A
Fc7: K326A/E333A
Fc8: K326M/E333A
Fc13: I332E TABLE 4-continued List of Fc variants
Name of Fc region: list of amino acids
modification with respect to native human
IgG1 Fc (called Fc0) of SEQ ID NO: 28

Fc14: S239D/I332E
Fc15: S298A/E333A
Fc16: E333A/K334A
Fc17: S298A/E333A/K334A
Fc20: F243L/R292P/Y300L/V305L/P396L
Fc21: K326A/E333A/D356E/L358M
Fc24: F243L/R292P/Y300L/V305L/K326A/E333A/P396L
Fc27: F243L/R292P/Y300L/V305L/D356E/L358M/P396L
Fc31: S298A
Fc32: K334A
Fc33: S298A/K334A
Fc34: F243L/R292P/Y300L/V305L/K326A/P396L
Fc35: S267E/H268F/S324T
Fc36: G236A/I332E
Fc37: G236A/S267E/H268F/S324T/I332E
Fc40: F243L/R292P/Y300L/V305I/K326A/P396L

Preferably, the antibodies of the invention (especially chimeric and humanized) may comprise a variant Fc selected from Fc7, Fc8, Fc15, Fc16, Fc20, Fc21, Fc24, Fc27, Fc34, Fc35, Fc37, Fc40.

Preferably, the antibodies of the invention (especially chimeric and humanized) may comprise the best variant Fc selected from Fc24 (SEQ ID NO: 32), Fc34 (SEQ ID NO: 34), Fc40 (SEQ ID NO: 36).

The antibodies, preferably monoclonal antibodies of the invention may be designated using the prefix R007 for any antibody comprising the murine paratope (antigen-binding site) of R007, preceded by "ch" for chimeric (the Fc regions of the murine has been replaced by a Fc specific for the treated species), or using the prefix Hz116 and Hz118 for any antibody having the respective humanized paratope. To this, we add the name of human IgG1 Fc region: Fc0 for the native one, or one of the optimized Fc depicted in Table 4. The other parts such as a Kappa region are not mentioned in the internal nomenclature; however, they may be present as appropriate. In particular, a human Kappa region may be present in the Light chain. In some preferred embodiment, objects of the present invention are chR007-Fc0, chR007-Fc24, chR007-Fc34, chR007-Fc40, Hz116-Fc0, Hz116-Fc24, Hz116-Fc34, Hz116-Fc40, Hz118-Fc0, Hz118-Fc24, Hz118-Fc34, Hz118-Fc40.

The following Table 5 is the "Sequence Information Table" regrouping the list of relevant amino acid and corresponding nucleic acid sequences in addition to the CDRs sequences disclosed supra, all of them being objects of the present invention.

| Identification | Amino Acids | Nucleotides | SEQ ID NO: |
|---|---|---|---|
| Murine VL | X | | 18 |
| Murine VL | | X | 19 |
| Murine VH | X | | 20 |
| Murine VH | | X | 21 |
| Humanized VL | X | | 22 |
| Humanized VL | | X | 23 |
| Humanized VH Hz116 | X | | 24 |
| Humanized VH Hz116 | | X | 25 |
| Humanized VH Hz118 | X | | 26 |
| Humanized VH Hz118 | | X | 27 |
| Human IgG1 Fc (Fc0) | X | | 28 |
| Human IgG1 Fc (Fc0) | | X | 29 |
| Human Kappa | X | | 30 |
| Human Kappa | | X | 31 |
| Fc24 | X | | 32 |
| Fc24 | | X | 33 |
| Fc34 | X | | 34 |
| Fc34 | | X | 35 |
| Fc40 | X | | 36 |
| Fc40 | | X | 37 |

Objects of the invention are the following antibodies, especially monoclonal antibodies and antigen-binding fragments thereof:

chR007-Fc0, which comprises a VL of SEQ ID NO: 18, a VH of SEQ ID NO: 20, a Fc of SEQ ID NO: 28, and possibly a Kappa of SEQ ID NO: 30. An antigen-binding fragment thereof comprises a VL of SEQ ID NO: 18, a VH of SEQ ID NO: 20.

chR007-Fc24, which comprises a VL of SEQ ID NO: 18, a VH of SEQ ID NO: 20, a Fc of SEQ ID NO: 32, and possibly a Kappa of SEQ ID NO: 30. An antigen-binding fragment thereof comprises a VL of SEQ ID NO: 18, a VH of SEQ ID NO: 20.

chR007-Fc34, which comprises a VL of SEQ ID NO: 18, a VH of SEQ ID NO: 20, a Fc of SEQ ID NO: 34, and possibly a Kappa of SEQ ID NO: 30. An antigen-binding fragment thereof comprises a VL of SEQ ID NO: 18, a VH of SEQ ID NO: 20.

chR007-Fc40, which comprises a VL of SEQ ID NO: 18, a VH of SEQ ID NO: 20, a Fc of SEQ ID NO: 36, and possibly a Kappa of SEQ ID NO: 30. An antigen-binding fragment thereof comprises a VL of SEQ ID NO: 18, a VH of SEQ ID NO: 20.

Hz116-Fc0, which comprises a VL of SEQ ID NO: 22, a VH of SEQ ID NO: 24, a Fc of SEQ ID NO: 28, and possibly a Kappa of SEQ ID NO: 30. An antigen-binding fragment thereof comprises a VL of SEQ ID NO: 22, a VH of SEQ ID NO: 24.

Hz116-Fc24, which comprises a VL of SEQ ID NO: 22, a VH of SEQ ID NO: 24, a Fc of SEQ ID NO: 32, and possibly a Kappa of SEQ ID NO: 30. An antigen-binding fragment thereof comprises a VL of SEQ ID NO: 22, a VH of SEQ ID NO: 24.

Hz116-Fc34, which comprises a VL of SEQ ID NO: 22, a VH of SEQ ID NO: 24, a Fc of SEQ ID NO: 34, and possibly a Kappa of SEQ ID NO: 30. An antigen-binding fragment thereof comprises a VL of SEQ ID NO: 22, a VH of SEQ ID NO: 24.

Hz116-Fc40, which comprises a VL of SEQ ID NO: 22, a VH of SEQ ID NO: 24, a Fc of SEQ ID NO: 36, and possibly a Kappa of SEQ ID NO: 30. An antigen-binding fragment thereof comprises a VL of SEQ ID NO: 22, a VH of SEQ ID NO: 24.

Hz118-Fc0, which comprises a VL of SEQ ID NO: 22, a VH of SEQ ID NO: 26, a Fc of SEQ ID NO: 28, and possibly a Kappa of SEQ ID NO: 30. An antigen-binding fragment thereof comprises a VL of SEQ ID NO: 22, a VH of SEQ ID NO: 26.

Hz118-Fc24, which comprises a VL of SEQ ID NO: 22, a VH of SEQ ID NO: 26, a Fc of SEQ ID NO: 32, and possibly a Kappa of SEQ ID NO: 30. An antigen-binding fragment thereof comprises a VL of SEQ ID NO: 22, a VH of SEQ ID NO: 26.

Hz118-Fc34, which comprises a VL of SEQ ID NO: 22, a VH of SEQ ID NO: 26, a Fc of SEQ ID NO: 34, and possibly a Kappa of SEQ ID NO: 30. An antigen-binding fragment thereof comprises a VL of SEQ ID NO: 22, a VH of SEQ ID NO: 26.

Hz118-Fc40, which comprises a VL of SEQ ID NO: 22, a VH of SEQ ID NO: 26, a Fc of SEQ ID NO: 36, and possibly a Kappa of SEQ ID NO: 30. An antigen-binding fragment thereof comprises a VL of SEQ ID NO: 22, a VH of SEQ ID NO: 26.

The CD5-binding fragments of antibody preferably comprises the 6 CDRs or the VH and VL regions of the parent whole antibody (murine, chimeric, humanized, etc. antibody). These fragments may be selected from: F(ab')$_2$, Fab, Fab', dsFv, (dsFv)$_2$, scFv, sc(Fv)$_2$, diabody, triabody, minibody, nanobody, scFv-Fc, multimeric scFv.

Compositions and Pharmaceutical Compositions

Another object of the invention is a composition or a pharmaceutical composition comprising at least one anti-CD5 antibody or CD5-binding fragment thereof, as disclosed and provided herein. The composition may further comprise a vehicle or diluent, in particular a vehicle or diluent suited to the intended use of the antibody. If the composition is a pharmaceutical composition, use is made of a pharmaceutically acceptable carrier, diluent or excipient.

The pharmaceutical compositions may comprise (i) at least one anti-CD5 antibody or antigen-binding fragment thereof, according to the invention, and (ii) at least one additional antibody directed against another target and/or at least one chemotherapeutic drug (such as small molecule). Both active principles may be present in the same composition. Or, these at least two active principles are separated, e.g. in separate vials or compositions. In an aspect, the composition comprises the at least two active principles for use in treating cancers, infections or autoimmune diseases as described herein, and/or for use in modulating immunity, for a simultaneous, separate or sequential administration to a mammal, including man.

As additional active principle, one may cite in particular doxorubicine, gemcitabine, camptothecin, paclitaxel. It may also be another antibody. The other antibody may be selected from the group consisting of another epitope on CD5, another cancer marker or receptor, another antigen expressed on immune competent cells, an immune checkpoint, a component involved in viral infection and a combination thereof. Thus in a particular embodiment, the pharmaceutical composition may comprise an anti-CD5 antibody or CD5-binding fragment thereof according to the invention, and another anti-CD5 antibody or CD5-binding fragment thereof.

Pharmaceutically acceptable carriers or excipients that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution.

In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be performed in a rectal suppository formulation (see above) or in a suitable enema formulation. Patches may also be used. The compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

For example, an antibody present in a pharmaceutical composition of this invention can be supplied at a concentration of 10 mg/mL in either 100 mg (10 mL) or 500 mg (50 mL) single-use vials. The product may be formulated for IV administration in 9.0 mg/mL sodium chloride, 7.35 mg/mL sodium citrate dihydrate, 0.7 mg/mL polysorbate 80, and Sterile Water for Injection. The pH may be adjusted to 6.5.

A pharmaceutical composition of the invention for injection (e.g., intramuscular, i.v.) could be prepared to contain a pharmaceutically acceptable carrier, diluent or excipient, e.g. sterile buffered water (e.g. 1 ml for intramuscular), and between about 1 ng to about 100 mg, e.g. about 50 ng to about 30 mg or more preferably, about 5 mg to about 25 mg, of anti-CD5 antibody or CD5-binding molecule according to the invention.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles that meet these requirements are contemplated for use in the present invention, and such particles may be are easily made. Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

For use, methods of use, use for the manufacture Unless inappropriate, all the features disclosed herein apply to the different objects of the invention, such as "for use", "methods of use" or "of treating", "use for the manufacture a medicament". In an embodiment, the patient or subject is a human.

Another object of the invention is an antibody, preferably monoclonal antibody, or an antigen-binding fragment thereof, or a pharmaceutical composition, as disclosed herein, for use as a medicament or drug.

The present invention relates to such CD5-binding antibodies or compositions containing the same, for use (i) as an anti-cancerous composition, (2i) as an immunomodulating composition, (3i) as anti-infectious composition, (4i) as an anti-inflammatory composition, or (5i) as a composition for treating an autoimmune disease. In particular, the immunomodulating effect may be helpful in treating or in the course of treating a cancer, an infection, an inflammation or an autoimmune disease. Thus, the present invention relates to such CD5-binding antibodies or compositions containing the same, for use as an immunomodulating and anti-cancerous composition, or as an immunomodulating, anti-inflammation and anti-infectious composition.

The present invention also relates to a method of treatment of cancer, especially cancer expressing CD5 or cancer comprising cells expressing CD5, comprising administering to a patient in need thereof a sufficient amount of such an antibody or antigen-binding fragment thereof, or a pharmaceutical composition comprising the same.

The present invention also relates to a method of treatment of a viral or bacterial infection, comprising administering to a patient in need thereof a sufficient amount of such an antibody or antigen-binding fragment thereof, or of such a pharmaceutical or immunomodulatory or anti-infectious composition.

The present invention also relates to a method of immunomodulation, comprising administering to a patient in need thereof a sufficient amount of such an antibody or antigen-binding fragment thereof, or of such a pharmaceutical or immunomodulatory composition.

In an embodiment according to the invention, the antibodies and fragments thereof as defined herein are intended for use in treating diseases expressing CD5 and/or to modulate the immune system by acting on CD5 positive cells, such as T conventional effector or T regulatory cells.

The antibody, preferably monoclonal antibody, or an antigen-binding fragment thereof, and the compositions may be used (e.g. "for use") in oncology, especially in treating a cancer or tumor. The invention particularly aims at treating cancers associated with CD5 expression or overexpression, preferentially cancer, preferably CD5 positive T leukemia cancer and CD5 positive lymphoma or solid cancers. Examples of such cancers include T leukemia, e.g. acute or chronic, Mantle cell lymphoma, liver cancer, hepatoma. Other cancers that may benefit from this treatment are disclosed herein.

In one aspect, the antibody by binding the inhibitory CD5 receptor triggers or participates to a control on immunosuppressive tumor environment with a beneficial therapeutic effect. For example, it may induce a downregulation of the intratumoral CD5 which may potentiate anti-tumor T cell responses following in situ sensitization tumor specific T lymphocytes (TIL). For example, it may induce inhibition of CD5+ B cells (which cells promote tumor growth by accelerating tumor angiogenesis) and/or sustain IL-10 production in tumor environment. For example, it may induce depletion and/or control of T reg CD5 positive cells to disrupt T cell anergy.

In an aspect, the method or the use leads to an inhibition of growth of a tumor cell expressing CD5. In an aspect, the method or the use leads to an inhibition and/or reversion of CD5-ligand binding, especially resulting in the inhibition of cancer cell proliferation or growth.

In an aspect, the method or the use leads to a modulation of immunosuppressive tumor environment. In an aspect, the method or the use leads to an inhibition and/or reversion of CD5-ligand binding, especially resulting in the inhibition of tumor tolerance.

In an aspect, the antibody, especially an antibody having an optimized Fc, may control the tumor growth by its CDC and/or ADCC functions. Advantageously, the antibodies of the invention allow control on immunosuppressive tumor environment and control of tumor growth.

The antibodies of the invention may be used for depleting CD5 expressing cancer cells in a cancerous subject, such as acute or chronic T leukemia or Mantle lymphoma cells. In some embodiments, the antibody triggers CDC induced cytotoxicity on CD5 positive cancer cells such as T leukaemia or Mantle cell lymphoma. In some embodiments, the antibody triggers ADCC induced cytotoxicity on CD5 positive cancer cells such as T leukaemia or Mantle cell lymphoma. In some embodiments, the antibody triggers both CDC and ADCC induced cytotoxicity on CD5 positive cancer cells such as T leukaemia or Mantle cell lymphoma. In those embodiments with CDC and/or ADCC functions, it is preferable to use antibodies of the invention having a variant (optimized) Fc region as described herein, especially the Fc24, Fc34 and Fc40 regions. As example, the antibody may be selected from the group consisting of chR007-Fc24, chR007-Fc34, chR007-Fc40, Hz116-Fc24, Hz116-Fc34, Hz116-Fc40, Hz118-Fc24, Hz118-Fc34, Hz118-Fc40.

In some embodiments, the antibody is used to control the immunosuppressive tumor environment and/or triggers anti-tumoral activity on CD5 positive leukemia cells, such as T-Cell Leukemia, T-Cell Acute Lymphocytic Leukemia, T-Cell Acute Lymphoblastic Leukemia, T-Cell Chronic Lymphocytic Leukemia, B-Cell Chronic Lymphocytic Leukemia.

In some embodiments, the antibody is used to control the immunosuppressive tumor environment and/or triggers anti-tumoral activity on CD5 positive lymphoma cells, such as T-Cell Lymphomas, Acute Lymphoblastic Lymphoma, Anaplastic Large Cell Lymphoma (ALCL), Non-Hodgkin Lymphoma, Hodgkin Lymphoma, Peripheral T-Cell Lymphomas (PTCL), Mantle Cell Lymphoma.

In an embodiment, the antibody is used to control the immunosuppressive tumor environment related to any cancer, not only CD5 positive cancer cells. In particular, the antibody controls Tumor infiltrating lymphocytes, infiltration, T conventional cell activation, and/or T regulatory cell modulation. Preferably, the antibody comprises the native IgG1 Fc (Fc0).

In an embodiment, the antibody is used to control the immunosuppressive tumor environment and/or triggers CDC induced cytotoxicity on CD5 positive cancer cells as disclosed herein, such as T leukaemia or Mantle cell lymphoma. Preferably, the antibody has an optimized Fc, such as Fc24, Fc34 or Fc40.

In an embodiment, the antibody is used to control the immunosuppressive tumor environment and/or triggers ADCC induced cytotoxicity and possibly CDC induced cytotoxicity on CD5 positive cancer cells as disclosed herein, such as T leukaemia or Mantle cell lymphoma. Preferably, the antibody has an optimized Fc, such as Fc24, Fc34 or Fc40.

In an embodiment, the antibody is used to optimize immunotherapy in oncology by controlling the immunosuppressive tumor environment by specifically blocking negative CD5 receptor cells as disclosed herein, such as Adoptive cell transfer therapy (ACT), Chimeric antigen receptor (CAR) T cell therapy. Preferably, the antibody has no optimized Fc.

In an embodiment, the antibody is used to improve Chimeric antigen receptor (CAR) T cell manufacturing, the antibody being used to remove and eliminate CD5 positive immunosuppressive cells during the cell preparation. In particular, the CDC function of the antibody contributes to this elimination. Preferably, the antibody has an optimized Fc, such as Fc24, Fc34 or Fc40.

As example, the antibody for use in oncology may be selected from the group consisting of chR007-Fc24, chR007-Fc34, chR007-Fc40, Hz116-Fc24, Hz116-Fc34, Hz116-Fc40, Hz118-Fc24, Hz118-Fc34, Hz118-Fc40.

The antibody, preferably monoclonal antibody, or an antigen-binding fragment thereof, and the compositions may be used (e.g. for use) in immunomodulation or in the modulation of the immune system.

The antibody may modulate immune cell proliferation and/or activation of T conventional effector cells.

The antibody may down modulate immune cell proliferation and/or activation of T regulatory cells.

A use may be triggering modulation of CD5 immune cells; as disclosed above, this may be beneficial in disease treatment, such as cancer treatment; this may be beneficial in bacterial and viral infections as well, such as tuberculosis (infection by *Mycobacterium tuberculosis*), or HCV infection; and this may be beneficial in the treatment of autoimmune diseases.

The antibody may thus be helpful in treating viral and bacterial infections. In an embodiment, the antibody may be used (e.g. for use) in treating HCV infection or tuberculosis infection or progression. The invention also relates to a method of treating Hepatitis C Virus (HVC) infection comprising administering to the subject a sufficient or therapeutically effective amount of an antibody of the present invention or an antigen-binding fragment thereof, or a composition according to the invention.

A use may be inhibiting HCV infection of CD5 T cells; or treating HCV infection, especially through inhibition of HCV infection of CD5 T cells. In an embodiment, the use inhibits HCV lympho-tropism and/or HCV propagating in the extrahepatic compartment.

The antibody may control Tuberculosis progression. Still another use may be treating tuberculosis, especially through modulation of CD5 immune cells. The invention also relates to a method of treating *Mycobacterium tuberculosis* infection comprising administering to the subject a sufficient or therapeutically effective amount of an antibody of the present invention or an antigen-binding fragment thereof, or a composition according to the invention.

Still another use may be treating an autoimmune disease, especially through modulation of CD5 immune cells. In an embodiment, the antibody or antigen-binding fragments thereof modulates immune responses according the cellular type targeting of CD5 positive cells. In an embodiment, the antibody or antigen-binding fragments thereof controls immune cell proliferation/activation of T conventional effector cells and/or of T regulatory cells. The invention also relates to a method of modulate immune response comprising administering to the subject a sufficient or therapeutically effective amount of an antibody of the present invention or an antigen-binding fragment thereof, or a composition according to the invention In some embodiments, the antibody modulates, and is used for modulating, CD5 positive cells in Anti-Neutrophil Cytoplasmic Antibody-Associated Vasculitis (ANCA Vasculitis), Vasculitis, Atopic Dermatitis (Atopic Eczema), Recurrent Abortion.

In each of the embodiments of the use and treatment methods described herein, the anti-CD5-binding antibody or molecule may be delivered in a manner consistent with conventional methodologies associated with management of the disease or disorder for which treatment is sought. In accordance with the disclosure herein, an effective amount of the CD5-binding antibody or molecule is administered to a patient in need of such treatment for a time and under conditions sufficient to treat the disease or disorder.

As used herein, the terms "treatment" and "treat" refer to curative or disease modifying treatment, including treatment of subjects who have cancer, or is diagnosed as suffering from cancer, especially CD5-expressing cancer, and includes suppression of clinical relapse. The treatment may concern a subject having a cancer, in order to cure, delay the onset of, reduce the severity of, or ameliorate one or more symptoms of said cancer, or in order to prolong the survival of a subject beyond that expected in the absence of such treatment.

As used herein, the terms "treatment" and "treat" refer to curative or disease modifying treatment, including treatment of subjects who have HCV infection or *Mycobacterium tuberculosis* infection or other viral or bacterial infection, and includes suppression of clinical relapse. The treatment may concern a subject having viral or bacterial infection, in order to cure, delay the onset of, reduce the severity of, or ameliorate one or more symptoms of infection, or in order to prolong the survival of a subject beyond that expected in the absence of such treatment.

As used herein, the terms "treatment" and "treat" refer to curative or disease modifying treatment, including treatment of subjects who have autoimmune diseases or is diagnosed as suffering from autoimmune diseases, and includes suppression of clinical relapse. The treatment may concern a subject having autoimmune diseases, in order to cure, delay the onset of, reduce the severity of, or ameliorate one or more symptoms of said autoimmune disease, or in order to prolong the survival of a subject beyond that expected in the absence of such treatment.

The disclosed antibodies or antigen-binding fragments thereof can be administered as a therapeutic agent to a subject, in particular a human, in amounts ranging from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 0.5 mg/kg to about 25 mg/kg, or from about 0.5 to about 10, 5, 3 or 2 mg/kg of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy of the treatment is monitored during the therapy, e.g. at predefined points in time. In some embodiments, the efficacy may be monitored by visualization of the disease area, or by other diagnostic methods described further herein, e.g. by performing one or more PET-CT scans, for example using a labelled antibody of the present invention, or an antigen-binding fragment thereof. If desired, an effective daily dose of a pharmaceutical composition may be administered as two, three, four, five, six or more sub-doses administered separately at appropriate intervals throughout the day, optionally, in unit dosage forms. In some embodiments, the monoclonal antibodies of the present invention are administered by slow continuous infusion over a long period, such as more than 24 hours, in order to minimize any unwanted side effects. An effective dose of an antibody of the present invention may also be administered using a weekly, biweekly or triweekly dosing period. The dosing period may be restricted to, e.g., 8 weeks, 12 weeks or until clinical progression has been established. As non-limiting examples, treatment according to the present invention may be provided to a subject, especially a human, as a daily dosage of an antibody of the present invention or an antigen-binding fragment thereof in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

In certain embodiments, an anti-CD5 antibody or an antigen-binding fragment thereof according to the invention is used in combination with a second agent for treatment of a disease or disorder. When used for treating cancer, viral or bacterial infectiology, autoimmune diseases, an antibody of the invention may be used in combination with conventional cancer therapies such as, e.g., surgery, radiotherapy, chemotherapy, with conventional anti-viral therapies, with antibiotics, with immuno-checkpoints or combinations thereof.

The present invention also relates to the use of such antibodies and antigen-binding fragments thereof for the manufacture of a pharmaceutical or anti-cancerous and/or immunomodulating composition for treating diseases, especially HCV infection, Tuberculosis development or CD5 positive cancers such as T leukemia or Mantle cell lymphoma.

Combination

The present invention also provides for therapeutic applications or methods of treatment where an antibody of the present invention or an antigen-binding fragment thereof is used in combination with at least one further therapeutic agent, e.g. for treating cancer, for treating virus or bacterial infections, and for treating autoimmune diseases. Such administration may be simultaneous, separate or sequential; i.e. treatment with the two active principles can be at the same time (e.g. simultaneously or concurrently), or at different times (e.g. consecutively or sequentially), or a combination thereof. The further therapeutic agent is typically relevant for the disorder to be treated. Exemplary therapeutic agents include other anti-cancer antibodies, cytotoxic agents, chemotherapeutic agents, anti-angiogenic agents, anti-cancer immunogens, cell cycle control/apoptosis regulating agents, hormonal regulating agents, and other agents described below.

In some embodiments, the antibody of the present invention or an antigen-binding fragment thereof is used in combination with a chemotherapeutic agent. The term "chemotherapeutic agent" refers to chemical compounds that are effective in inhibiting tumor growth.

In some embodiments, the antibody of the present invention or an antigen-binding fragment thereof is used in combination with anti-viral agents, antibiotics or other agents used for the treatment of viral or bacterial infectiology.

In some embodiments, the antibody of the present invention or an antigen-binding fragment thereof is used in combination with immune-modulator agents, or other agents used for the treatment of autoimmune diseases.

Targeting CD5 with the antibodies of the present invention or an antigen-binding fragment thereof in combination with existing chemotherapeutic treatments will be more effective in killing the tumor cells than chemotherapy alone. Examples include, but are not limited to, cisplatin, taxol, etoposide, mitoxantrone, actinomycin D, campthotecin, methotrexate, gemcitabine, mitomycin, dacarbazine, 5-fluorouracil, doxorubicine and daunomycin.

The antibodies of the invention or antigen-binding fragments thereof may be used in combination with Immune Check Point Inhibitors as further anti-cancer agent, such as anti-PD1, anti-PD-L1 or anti-CTLA4 antibodies.

In one approach, the CD5-binding antibody or molecule is added to a standard chemotherapy regimen, in treating a cancer patient. For those combinations in which the antibody or an antigen-binding fragment thereof and additional anti-cancer agent(s) exert a synergistic effect against cancer cells, the dosage of the additional agent(s) may be reduced, compared to the standard dosage of the second agent when administered alone. The antibody or an antigen-binding fragment thereof may be co-administered with an amount of an anti-cancer drug that is effective in enhancing sensitivity of cancer cells to the antibody combination.

In one method of the invention, the CD5-binding antibody or molecule is administered to the patient prior to administration of a second anti-cancer agent. One alternative method comprises administering the second anti-cancer agent prior to administering the CD5-binding antibody or molecule and second agent on an alternative schedule. In another embodiment, the CD5-binding antibody or molecule and second agent are administered simultaneously.

The method of the invention may provide for the inclusion in a therapeutic regimen involving the use of at least one other treatment method, such as irradiation, chemotherapy with small molecule or antibody. The method of the invention may directly include the administration of a sufficient amount of at least one additional antibody directed against another target and/or at least one chemotherapeutic drug (such as small molecule), for a simultaneous, separate or sequential administration with antibody(ies) of the invention, or antigen-binding fragment(s) thereof, to a mammal, including man. As additional active principle, one may cite doxorubicine, gemcitabine, camptothecin, paclitaxel, and the other drugs mentioned above. In an embodiment, acute or chronic T leukemia, Mantle cell lymphoma, as well as other cancers mentioned above are treated using such combination. This combination more generally is useful for cancers (in particular aggressive cancers) which do not respond well to treatment with the drug alone or the antibodies/antibody of the invention or antigen-binding fragment thereof alone, and for which the combination leads to a synergistic effect.

Targeting CD5 with the antibodies of the present invention or an antigen-binding fragment thereof in combination with existing anti-viral treatments will be more effective in HCV infection progression than anti-viral treatments including antibiotic, antifungal and anti-parasitic drugs alone, or antiviral drugs based on antibodies alone. A wide variety of drugs have been employed in autoimmune diseases related therapies.

Targeting CD5 with the antibodies of the present invention or an antigen-binding fragment thereof in combination with existing anti-bacterial treatments, such as against tuberculosis, will be more effective in *Mycobacterium* infection progression than those anti-bacterial treatments alone. A wide variety of drugs have been employed in autoimmune diseases related therapies.

Targeting CD5 with the antibodies of the present invention or an antigen-binding fragment thereof in combination with existing autoimmune disease treatments will be more effective in autoimmune disease progression than these treatments alone. A wide variety of drugs have been employed in autoimmune diseases related therapies.

Additional Definitions

The term "antibody" is used in the broadest sense and specifically covers intact or whole monoclonal antibodies, and derived antibodies and antibody fragments as disclosed herein, so long as they exhibit the desired biological activity, as defined herein.

"Native antibodies" and "native immunoglobulins" are usually glycoproteins of about 150,000 daltons, composed of two identical Light (L) Chains and identical Heavy (H) Chains. Each Light Chain is linked to a Heavy Chain by one covalent disulfide bond, while the number of disulfide linkages varies among the Heavy Chains of different immunoglobulin isotypes. Each Heavy and Light Chain also has regularly spaced intrachain disulfide bridges. Each Heavy Chain has at one end a variable domain (VH or $V_H$). Each Light Chain has at one end a variable domain (VL or $V_L$).

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light Chains are classified as either kappa or lambda. Heavy Chains are classified as gamma, mu, alpha, delta, or epsilon, which in turn define the immunoglobulin classes, IgG, IgM, IgA, IgD and IgE, respectively.

With respect to antibodies of the invention, the term "specifically binds" refers to antibodies that bind to one or more epitopes of CD5, but which do not substantially recognize and bind other molecules in a sample containing a mixed population of antigenic biological molecules.

"Antibody fragments" comprise a portion of an intact antibody, which comprises at least the antigen-binding or variable region of the intact antibody. A suitable "antibody fragment" is a fragment of antibody that has the capability to bind to the CD5 binding region or epitope specifically recognized by the murine parental R007 antibody and keep or substantially keep the antigen-binding property of the intact R007 antibody (parental murine or derived forms thereof, i.e. chimeric or humanized). More particularly, the fragments keep or substantially keep the biological property of the intact (full-size) antibody.

The antibodies specifically binding to CD5 comprise one or two, preferably two, binding domains comprising a pair of VH and VL chains comprising the six CDRs of murine monoclonal antibody (R007), as disclosed in Table 1 supra, or of Humanized R007 antibodies, as disclosed in Tables 2 and 3 supra. Preferably, each one of these antibodies comprise two identical VH and VL chains as disclosed.

These antibodies binds specifically to an epitope or a binding region on the CD5 antigen, and as disclosed herein, the epitope or binding region is deemed conformational. The CDRs in Table 1 originate from a murine antibody. These antibodies according to the invention may be fully murine and this is a first series of embodiments. In other embodiments, these antibodies are chimeric antibodies wherein part of the antibody is human and more particularly the murine VH and VL regions are combined to human sequences to complete the whole Heavy and Light Chains, and retain or substantially retain the antigen-binding properties of the parental murine antibody. In another embodiment, these antibodies are humanized antibodies, wherein these humanized antibodies or binding fragments thereof comprise the same set of 6 CDRs in their respective VH and VL regions with humanized framework (FR) regions, and retain or substantially retain the antigen-binding properties of the parental murine antibody. In still another embodiment, these humanized antibodies or binding fragments thereof further comprise some mutations or amino acid changes in at least one CDR of the set of six.

The CD5 antigen is expressed on different types of immune cells such as T effector conventional cells (CD4+ CD3+Foxp3−) or T regulatory cells (CD4+CD3+Foxp3+). Therefore, the anti-CD5 antibody or antigen-binding fragment thereof is capable to modulate immunological pathways, directly or indirectly, substantially activating, counteracting, reducing or inhibiting CD5 biological activity. By contrast, on another cell type expressing CD5, the fragment is capable of, directly or indirectly, substantially acting as CD5 ligand mimicking CD5 activation following molecular interaction between CD5 and its CD5 ligand(s). Optionally, the fragment is capable of neutralizing the formation of a complex between CD5 and virus, such as Hepatitis Virus C, inhibiting therefore HCV lymphotropism and HCV propagating in this extrahepatic compartment.

The terms "polypeptide", "peptide" and "protein" are used interchangeably herein to refer to a polymer of amino acid residues. The terms apply to naturally occurring amino acid polymers as well as to amino acid polymers in which one or more amino acid residues is an artificial chemical analogue of a corresponding naturally occurring amino acid. The term also includes variants on the traditional peptide linkage joining the amino acids making up the polypeptide. Preferred "peptides", "polypeptides", and "proteins" are chains of amino acids whose carbons are linked through peptide bonds. Peptides also include essentially any polyamino acid including, but not limited to peptide mimetics such as amino acids joined by ether as opposed to an amine bond.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated, in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (Kabat et al., *NIH Publ.* 1991; No. 91-3242, Vol. 1, 647-669). The constant domains are not involved directly in binding an antibody to an antigen, but exhibit various effectors functions, such as participation of the antibody in antibody-dependent cellular toxicity.

The monoclonal antibodies herein specifically include "chimeric" antibodies (immunoglobulins) in which a portion of the Heavy and/or Light Chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)).

Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L et al., *Proc. Natl. Acad. Sci. USA* 1984; 81:6851-6855; U.S. Pat. Nos. 5,202,238 and 5,204,244. WO 2006/093794 relates to heterodimeric protein binding compositions. WO 99/37791 describes multipurpose antibody derivatives. Morrison et al., the *J. Immunolog.* 1998; 160:2802-2808 refers to the influence of variable region domain exchange on the functional properties of IgG.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementarity-determining region (CDR) of the recipient are replaced by residues from a CDR of a non-human species (donor antibody) which is mouse herein, having the desired specificity, affinity, and capacity.

In a preferred embodiment, a murine CDR is grafted into the framework region of a human antibody to prepare the "humanized antibody". See, e.g., Riechmann, L. et al., *Nature.* 1988; 332: 323-327; and Neuberger, M S et al., *Nature.* 1985; 314: 268-270. Particularly preferred CDRs correspond to those representing sequences recognizing the antigens noted above for chimeric antibodies.

Other forms of "chimeric antibodies" or "humanized antibodies" encompassed by the present invention are those in which the constant region has been additionally modified or changed from that of the original antibody to generate the properties according to the invention, especially in regard to C1q binding and/or Fc receptor (FcR) binding.

Furthermore, humanized antibodies may comprise residues that are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature.* 1986; 321:522-525; Reichmann et al., *Nature.* 1988; 332:323-329; and Presta et al., *Curr. Op. Struct. Biol.* 1992; 2:593-596.

Humanized antibodies, or antibodies adapted for non-rejection by other mammals, may be produced using several technologies such as resurfacing and CDR grafting. As used herein, the resurfacing technology uses a combination of molecular modeling, statistical analysis and mutagenesis to alter the non-CDR surfaces of antibody variable regions to resemble the surfaces of known antibodies of the target host. Antibodies can be humanized using a variety of other techniques including CDR-grafting (EP0239400; WO91/09967; U.S. Pat. Nos. 5,530,101 and 5,585,089), veneering or resurfacing (EP0592106; EP0519596; Padlan (1991) *Molecular Immunology* 28(4/5):489-498; Studnicka et al. (1994) *Protein Engineering* 7(6):805-814; Roguska et al. (1994) *Proc. Natl. Acad. Sci U.S.A.* 91:969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814,318; and International patent application WO98/46645, WO98/50433, WO98/24893, WO98/16654, WO96/34096, WO96/33735, and WO91/10741.

The mechanism of action of MAbs is complex and appears to vary for different MAbs. There are multiple mechanisms by which MAbs cause target cell death. These include apoptosis, complement dependent cytotoxicity (CDC), antibody dependent cytotoxicity (ADCC) or inhibition of signal transduction.

"Treatment" or "therapy" refer to both therapeutic treatment and prophylactic or preventative measures. Preferably, it is therapeutic treatment.

"Mammal" for purposes of treatment or therapy refers to any animal classified as a mammal, including humans, domestic and farm animals, and zoo, sports, or pet animals, such as dogs, horses, cats, cows, etc. Preferably, the mammal is human. Except indicated to the contrary, the terms "subject", "patient" and the like include mammals including human.

The terms "cancer" and "cancerous" refer to or describe the physiological condition in mammals that is typically characterized by unregulated cell growth.

The term "nucleic acid" or "oligonucleotide" or grammatical equivalents herein refer to at least two nucleotides covalent linked together. A nucleic acid of the present invention is preferably single-stranded or double stranded and will generally contain phosphodiester bonds.

Amino acid sequence "variants" (or mutants) of the antibody are prepared by introducing appropriate nucleotide changes into the antibody DNA, or by nucleotide synthesis. Such modifications can be performed, however, only in a very limited range, e.g. as described herein. For example, the modifications do not alter the above-mentioned antibody characteristics such as the IgG isotype and antigen-binding, but may improve the yield of the recombinant production, protein stability or facilitate the purification.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98% or 99%, sequence identity to the native (endogenous) nucleotide sequence.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 95, 100%, or any amount of reduction in between as compared to native or control levels.

Chimeric antigen receptor (CAR) T cell therapy has provided patients with relapsed/refractory B cell malignancies a new therapeutic option, but this class of therapeutics has not demonstrated consistent therapeutic benefit in solid tumors. The CAR T antitumor efficacy may depend on several factors including the design of the CAR construct, the quality of T cells for CAR T manufacturing, the manufacturing process, the lymphodepletion regimen, infused cell phenotype, and the tumor burden and tumor microenvironment. These approaches include next-generation CAR T cell engineering to overcome to mitigate T cell exhaustion and to prevent suppression by the Tumor microenvionnement (TME), as well as novel approaches for regional delivery to facilitate tumor T cell trafficking. Adoptive cell transfer therapy (ACT) is an immunotherapy that separates immunocompetent cells from cancer patients and transfers them to patients after expansion or functional identification in vitro; adoptive cells kill tumor cells directly or stimulate the body's immune response.

Production of Antibodies

The antibodies of the present invention and antigen-binding fragments thereof are produced by any technique known in the art, such as, without limitation, any chemical, biological, genetic or enzymatic technique, either alone or in combination. Typically, knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, California) and following the manufacturer's instructions. Alternatively, antibodies of the present invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Mammalian cells are the preferred hosts for production of therapeutic antibodies, due to their capability to glycosylate proteins in the most compatible form for human applications. Bacteria very rarely glycosylate proteins, and like other type of common hosts, such as yeasts, filamentous fungi, insect and plant cells yield glycosylation patterns associated with rapid clearance from the blood stream.

Among mammalian cells, Chinese hamster ovary (CHO) cells are the most commonly used. In addition to giving suitable glycosylation patterns, these cells allow consistent generation of genetically stable, highly productive clonal cell lines. They can be cultured to high densities in simple bioreactors using serum-free media, and permit the development of safe and reproducible bioprocesses. Other commonly used animal cells include baby hamster kidney (BHK) cells, NSO— and SP2/0-mouse myeloma cells.

In an embodiment, the antibodies according to the invention are produced or expressed in mammal cells, preferably wild-type mammal cells, preferably of rodent origin, especially CHO cells.

Modifications and changes may be made in the structure of an antibody of the present invention and still obtain a molecule having like characteristics. For example, certain amino acids can be substituted for other amino acids in a sequence without appreciable loss of activity. Because it is the interactive capacity and nature of an antibody that defines that antibody's biological functional activity, certain amino acid sequence substitutions can be made in an antibody sequence (or, of course, its underlying DNA coding sequence) and nevertheless obtain an antibody with like properties.

In making such changes, the hydropathic index of amino acids can be considered. The importance of the hydropathic amino acid index in conferring interactive biologic function on an antibody is generally understood in the art. It is known that certain amino acids can be substituted for other amino acids having a similar hydropathic index or score and still result in an antibody with similar biological activity. Each amino acid has been assigned a hydropathic index on the basis of its hydrophobicity and charge characteristics.

It is believed that the relative hydropathic character of the amino acid determines the secondary structure of the resultant antibody, which in turn defines the interaction of the antibody with other molecules, for example, enzymes, substrates, receptors, antibodies, antigens, and the like. It is known in the art that an amino acid may be substituted by another amino acid having a similar hydropathic index and still obtain a biologically functionally equivalent polypeptide. In such changes, the substitution of amino acids whose hydropathic indices are within ±2 is preferred, those which are within ±1 are particularly preferred, and those within +0.5 are even more particularly preferred.

Substitution of like amino acids can also be made on the basis of hydrophilicity, particularly where the biologically functionally equivalent peptide or polypeptide thereby created is intended for use in immunological embodiments. U.S. Pat. No. 4,554,101, incorporated herein by reference or to which the person skilled in the art: may refer, states that the greatest local average hydrophilicity of a polypeptide, as governed by the hydrophilicity of its adjacent amino acids, correlate with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent, polypeptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like.

Amino acid substitution may be chosen or selected differently. Possible substitutions have been documented in WO99/51642, WO2007024249 and WO2007106707.

By definition, the CDRs of the invention include variant CDRs, by deletion, substitution or addition of one or more amino acid(s), which variant keeps the specificity of the original CDR and the whole VH+VL or antibody, substantially keeps the antigen-binding of the parental Fab or antibody.

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention. Another type of framework modification involves mutating one or more residues within the framework region, or even within one or more CDR regions, to remove T cell–epitopes to thereby reduce the potential immunogenicity of the antibody. This approach is also referred to as "deimmunization" and is described in further detail in U.S. Patent Publication No. 20030153043 by Carr et al.

Nucleic Acids and Vectors

The isolated nucleic acid sequences disclosed and provided herein are also object of the invention. Thus the invention also relates to an isolated nucleotide sequence selected from the group consisting of the nucleotide sequences SEQ ID NO: 19, 21, 23, 25, 27, 37 and more particularly combinations or sets of two nucleotide sequences separated or linked together: SEQ ID NO: 19 and 21, 23 and 25, 23 and 27, 21 and 33, 21 and 35, 21 and 37, 25 and 33, 25 and 35, 25 and 37, 27 and 33, 27 and 35, 27 and 37.

As mentioned above, methods for producing the antibodies are known from the person skilled in the art. The mammal cells, preferably rodent cells such as CHO cells, preferably wild-type cells are transfected with one or several expression vectors. Preferably, the cells are co-transfected with an expression vector for light chain and with an expression vector for heavy chain. Cell transfection is also known from the person skilled in the art. As transfection that may be performed, one may mention without limitation standard transfection procedures, well-known from the man skilled in the art, such as calcium phosphate precipitation, DEAE-Dextran mediated transfection, electroporation, magnetofection, nucleofection (AMAXA Gmbh, GE), liposome-mediated transfection (using Dreamfect®, Lipofectin® or Lipofectamine® technology for example) or microinjection.

Expression vectors are known. As vectors that may be used, one may mention without limitation: pcDNA3.3, pOptiVEC, pFUSE, pMCMVHE, pMONO, pSPORT1, pcDV1, pcDNA3, pcDNA1, pRc/CMV, pSEC. One may use a single expression vector or several expression vectors expressing different parts of the antibody.

The invention also relates to an expression vector encoding a Heavy Chain of an anti-CD5 antibody, an expression vector encoding a Light Chain of an anti-CD5 antibody, or an expression vector encoding a Heavy Chain and a Light Chain of an anti-CD5 antibody.

Another object of the invention is a host cell containing a vector or a set of vectors of the invention. The host cell may be a mammal cell, preferably a rodent cell, more preferably CHO cell. Still more preferably, the host cell may be a wild-type mammal cell, preferably a wild-type rodent cell, most preferably a wild-type CHO cell.

The person skilled in the art fully owns the methods to generate the antibodies according to the invention using such a vector or vectors and cells such as CHO cells.

BRIEF DESCRIPTION OF THE DRAWINGS

FIG. 12: Amino acid and nucleic acid sequence for murine or chimeric VH R007 with description of the FR1, CDR1, FR2, CDR2, FR3, CDR3 defined according to IMGT (SEQ ID NO: 20)

FIG. 13: Amino acid and nucleic acid sequence for murine or chimeric VL R007 with description of the FR1, CDR1, FR2, CDR2, FR3, CDR3, defined according to IMGT (SEQ ID NO: 18).

FIG. 14: Amino acid and nucleic acid sequence for 7Hz116 humanized VH with description of the FR1, CDR1, FR2, CDR2, FR3, CDR3, defined according to IMGT (SEQ ID NO: 24).

FIG. 15: Amino acid and nucleic acid sequence for 7Hz116 humanized VL with description of the FR1, CDR1, FR2, CDR2, FR3, CDR3, defined according to IMGT (SEQ ID NO: 22).

FIG. 16: Amino acid and nucleic acid sequence for 7Hz118 humanized VH with description of the FR1, CDR1, FR2, CDR2, FR3, CDR3, defined according to IMGT (SEQ ID NO: 26).

FIG. 17: Amino acid and nucleic acid sequence for Contant Kappa light chain (SEQ ID NO: 30).

FIG. 18: Amino acid and nucleic acid sequence for Constant IgG1 (Fc0) wild type chain (SEQ ID NO: 28).

FIG. 19: Amino acid and nucleic acid sequence for Constant IgG1 Fc24 chain.

FIG. 20: Amino acid and nucleic acid sequence for Constant IgG1 Fc34 chain.

FIG. 21: Amino acid and nucleic acid sequence for Constant IgG1 Fc40 chain.

EXAMPLES

Figure 1:
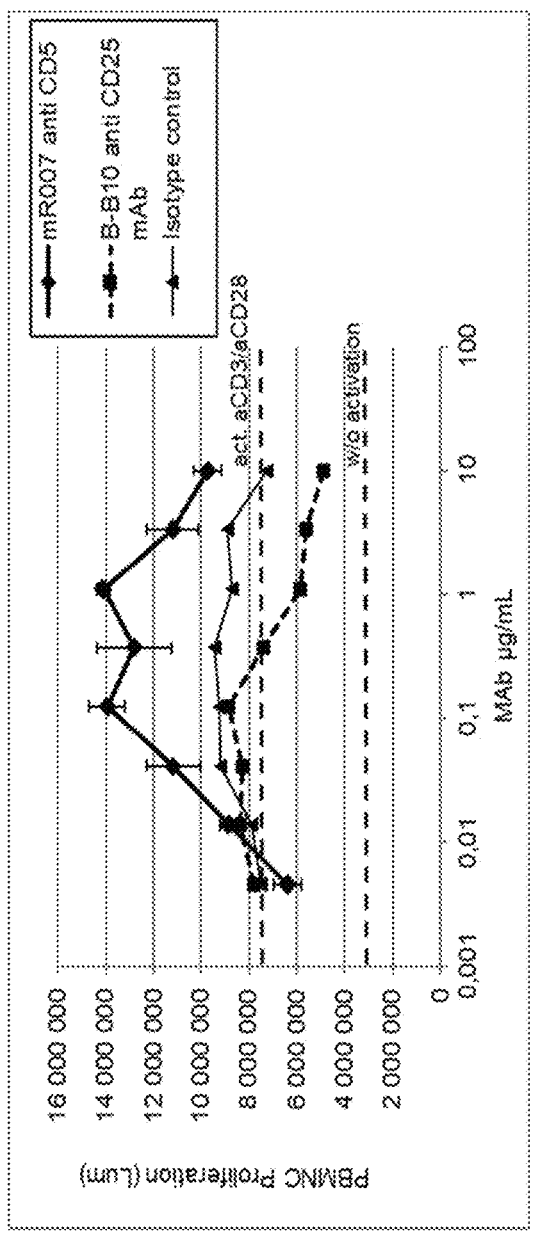
FIG. 1: The presence of MAb mR007 enhances Peripheral Blood Mononuclear cells (PBMNC) stimulation induced with MAb anti-CD3 and anti-CD28 MAbs, (Representative experiment on 3 independent experiments).

The following examples are offered to illustrate, but not to limit the claimed invention.

Example 1: Preparation of Murine Anti-CD5 Antibody

This example illustrates the preparation of hybridoma cell lines secreting anti-CD5 antibodies. The murine monoclonal antibodies specific for CD5 were produced using standard hybridoma techniques (Zola et al., Aust J. Exp Biol Med Sci. 1981; 59:303-6). After hybridoma cloning, one murine MAb was obtained called R007 (also named B—B8, Diaclone, France). The clone was injected into the peritoneum of nude mice. Protein A chromatography from murine ascitic fluid. The murine ascitic fluid is adjusted at pH 8.3 with the equilibration buffer 0.1 M Tris and 1.5 M Sulfate Ammonium and then loaded onto the rProtein A Sepharose Fast Flow column (GE Healthcare, Saint Cyr au Mont d'or, France). The non-binding proteins are flowed through and removed by several washings with equilibration buffer. The anti-CD5 monoclonal antibody (MAb anti-CD5) is eluted off the Protein A column using the elution buffer 0.1 M Citrate Sodium at pH 3.5. After concentration, the PBS solution containing IgG was filtered and the MAb concentration was determined at 280 nm.

A chimeric version of the murine parental R007 was produced as disclosed herein to get the chR007 monoclonal antibody made of a Heavy chain comprising the murine VH region of SEQ ID NO: 20 and a human IgG1 Fc of SEQ ID NO: 28, and of a Light chain comprising the murine VL region of SEQ ID NO: 18 and a human Kappa region of SEQ ID NO: 30.

Example 2: Cell Culture

Various tumor-derived cell lines are among the target cells that may be stained with MAb anti-CD5, in such assay procedures.

Cell lines. The established human CD5 positive acute lymphoblastic T leukemia cell line (ALL) CEM (available from ATCC) was grown in RPMI-1640 Medium (Sigma, St Quentin Fallavier, France) supplemented with 10% heat-inactivated fetal bovine serum (FBS) (Sigma, St Quentin Fallavier, France), 4 nM L-glutamine (Sigma, St Quentin Fallavier, France) and 100 U/mL, 100 μg/mL penicillin—streptomycin (Sigma, St Quentin Fallavier, France). The established human CD5 positive Mantle Cell Lymphoma (MCL) NCBE-1 (ATCC® CRL-3005™) was grown in RPMI-1640 Medium (Sigma, St Quentin Fallavier, France) supplemented with 10% heat-inactivated fetal bovine serum (FBS) (Sigma, St Quentin Fallavier, France), 4 nM L-glutamine (Sigma, St Quentin Fallavier, France) and 100 U/mL, 100 µg/mL penicillin—streptomycin (Sigma, St Quentin Fallavier, France).

Example 3: CD3*CD28 Co-Stimulation Assay

Peripheral Blood Mononuclear Cells (PBMCs) were cultured ($2.10^5$ cells/well) in RPMI1640 supplemented by FCS 10%, L-Glutamine 4 mM, penicillin 10 U/mL, streptomycin 100 µg/mL. The experiment was done in 96 wells culture plates coated with 100 µL/well of anti-CD3 and anti-CD28 antibodies (0.1 µg/mL each) overnight at +4° C. All was done in triplicate conditions. The final volume in the culture plate was 200 µL/well. Serial antibodies concentrations were tested. The plates were incubated during 72 h at 37° C. with 5% $CO_2$. ATPlite was added and the luminescence was measured.

Example 4: Complement Binding Assay

The Binding of Human C1q to MAbs was assessed by an ELISA binding assay. The 96-well plates (Nunc) were coated overnight at 4° C. with varying MAb concentrations. After washing, the plates were blocked with PBS-5% BSA for 1 h, and incubated for 1 h with 0.2 µg/ml of recombinant human C1q (Abd Serotec) or 2.5 µl of natural human complement (Sigma). Then, 100 µl of a 1/500 dilution of sheep anti-human C1q peroxidase-conjugated Ab (Abd Serotec) added and incubated for 1 h. The plates were developed with 100 µl per well of TMB substrate (Uptima Interchim). After $H_2SO_4$ addition, the OD was measured at 450 nm/630 nm using a MRX II microplate reader.

Example 5: Complement Dependent Cytoxicity Assay (CDC)

Target cells (50 000 cells per well) such as T leukemia CEM or Mantle lymphoma NCEB-1 were incubated with various MAb concentration. Then, rabbit serum was added the culture and then cells were incubated 4 hours at +37° C. under shaking condition. At the end of incubation, lactate deshydrogenase present in supernatant was measured with LDH assay kit (Promega, France). Fluorescence was recorded at the 590 nm excitation wavelength. Specific lysis was calculated using the formula above: (experimental release–target spontaneous release)/(maximal release–target spontaneous release)*100, where target and effector cells without antibody represented spontaneous release. Maximal release value was obtained by treating target cells with Triton X-100.

Example 6: Antibody Dependent Cell Cytoxicity Assay (ADCC)

Primary cells such as T leukemia CEM or Mantle lymphoma NCEB-1 used as target cells were loaded with 12.5 µM Calcein-AM dye (Sigma, France). 5 000 target cells per well were the pre-incubated with different concentration of interest MAbs and controls for 20 min at +4° C. The isolated peripheral blood mononuclear (PBMNC) effector cells were then added to the target cells at the ratio E/T equal to 50:1. Specific lysis was calculated using the formula above: (experimental release–(spontaneous release Target+Effector))/(maximal release–spontaneous release target)*100, where target and effector cells without antibody represented spontaneous release. Maximal release value was obtained by treating target cells with Triton X-100.

Example 7: Preparation of Chimeric Monoclonal Antibody Directed Against CD5

DNA encoding the monoclonal antibodies is readily isolated and sequenced using conventional procedures (e.g. by using oligonucleotide probes that are capable of binding specifically to genes encoding the heavy and light chains of murine antibodies).

The cDNA corresponding to the variable region of the hybridoma was obtained using two approaches. The first approach consisted in the use in PCR of the degenerate N-term amino acid related primer set generated from the N-Terminal sequencing. The second approach consisted in the use in PCR of degenerate primer set generated by IMGT® primer database and specific primers previously described (Essono et al., *J Immunol Methods*. 2003; 203: 279:25-66, Wang et al., *Mol Immunol*. 1991; 28:1387-97). The sequence of N-terminal variable region was determined by Edman degradation. Total RNA extraction was carried out using the Tri Reagent kit according to the protocol described by the supplier Sigma. The amplified VL and VH fragments were cloned into the TOPO-TA cloning vector (Invitrogen) for sequence analyses by the dideoxytermination method (Sanger et al., *Nature*. 1977; 265:687-95). Then antibody variant constructs were amplified by PCR and cloned into the expression vector.

Positions were numbered according to IMGT and to Kabat index (Identical V region amino acid sequences and segments of sequences in antibodies of different specificities). Relative contributions of VH and VL genes, minigenes, and complementarity-determining regions to binding of antibody-combining sites were analyzed (Kabat et al., *NIH Publ*. 1991; No. 91-3242, Vol. 1, 647-669).

Example 8: Preparation of Fc Optimized Monoclonal Antibodies

Substitutions in the Fc domain were introduced using "megaprimer" method of site-directed mutagenesis (Sarkar et al., 1990). Positions are numbered according to the Kabat index (Identical V region amino acid sequences and segments of sequences in antibodies of different specificities). Relative contributions of VH and VL genes, minigenes, and complementarity-determining regions to binding of antibody-combining sites were analyzed (Kabat et al., 1991). Heavy and light chain constructs were co-transfected into CHO DG44 (ATCC) suitable for MAb screening. Antibodies were purified using protein A affinity chromatography (GE Healthcare).

Example 9: Preparation of Humanized Monoclonal Antibodies

Antibody CDR and FR regions have been determined according to various numbering approaches such as IMGT (ImMunoGeneTics Information SystemR http://imgt.cines.fr), Kabat or Common Numbering System. However, IMGT determined CDRs for a given antibody are not necessarily identical to the CDRs defined by the other numbering systems. The CDRs and framework regions (FR) have been identified by the inventor thanks to IMGT numbering systems. (ImMunoGeneTics Information SystemR http://imgt.cines.fr).

Conversion of chimeric MAb to Humanized MAb:

Humanized CD5 antibody Heavy (H) and Light (L) chain were generated using CDR-grafting by the PCR method. In order to generate a humanized antibody in which the CDRs of a mouse monoclonal antibody are grafted onto a human antibody, there is preferably a high homology between the variable region of a mouse monoclonal antibody and the variable region of a human antibody. Thus, the H chain and L chain V regions of a mouse anti-human CD5 monoclonal antibody are compared to the V region of all known human antibodies using the software IMGT/DomainGapAlign. When a mouse antibody is humanized by a conventional technology, the amino acid sequence of some of the V region FRs of a mouse antibody supporting the CDR may be grafted onto the FR of a human V region, as desired. Then the sequence of the Humanized variable region of is determined. The variables regions of H and L were amplified by PCR and cloned into the expression vector p3U containing the human IgG1 constant region.

Two humanized antibodies were selected sharing a common light chain, but with distinct heavy chains:

monoclonal antibody 7Hz116 comprising a Heavy chain comprising a VH region of SEQ ID NO: 24 and a human IgG1 Fc region, and a Light chain comprising a VL region of SEQ ID NO: 23, and a human Kappa region of SEQ ID NO: 30; and monoclonal antibody 7Hz118 comprising a Heavy chain comprising a VH region of SEQ ID NO: 26 and a human IgG1 Fc region, and a Light chain comprising a VL region of SEQ ID NO: 23, and a human Kappa region of SEQ ID NO: 30.

Example 10: In Vivo Proof of Concept

Human cell line related to acute T leukemia (Cem cell line) or to Mantle lymphoma (NCBE-1 cell line) was subcutaneously injected in SCID mice, with a concentration of $5.10^6$ cells per injection (200 µL). Mice were randomized when the tumors reached a mean volume of about 100 mm³. All the mice were observed in order to detect any toxic effects of the product. The endpoint was defined by animal ethics as a tumor diameter of >18 mm, significant weight loss or alteration of animal well-being. In order to assess the effectiveness of the compounds on tumorigenesis, tumor volume was measured two times a week. The sizes of the primary tumors were measured using calipers and the tumor volume (TV) was extrapolated to a sphere using the formula TV=4/3 πxr³, by calculating the mean radius from the two measurements. The median and standard deviation were also calculated for each group. Median is preferred to mean in order to exclude the extreme values. MAb treatment was administered by intraperitoneal injection once time per week during three weeks at 100, 60, 30, 10 or 1 mg/kg doses. The product was prepared in accordance with the sponsor's guidelines, i.e. diluted in PBS. The endpoints were defined by clinical trial ethics as a tumor diameter of >18 mm or weight loss of >10% of body weight, or when the tumors are dangerous for mice (necrosis). Statistical analysis was performed with GraphPad Prism software. GraphPad Prism combined scientific graphing, comprehensive curve fitting, understandable statistics, and data organization. The t-test (two-tailed test) was performed on the tumor volume values (mm³) measured on the day of sacrifice.

Results

Immunomodulation in the Presence of the MAb mR007

The presence of the murine MAb mR007 enhances PBMNC stimulation induced with anti-CD3 and anti-CD28 MAbs (FIG. 1).

Chimerisation of the Murine MAb R007

In comparison with the IMGT database, the CDR sequences (Table 1) and full sequences of VL mR007 and of VH mR007 were determined (FIG. 13, respectively 12). The authenticity of the VH and VL sequences obtained by cDNA cloning were also confirmed by N-terminal amino acid sequencing of the target mouse monoclonal antibody. Heavy and light chains were separated before amino acid sequencing by polyacrylamide gel electrophoresis under reducing conditions and the 20 first amino were sequenced by Edman degradation. The sequences were then cloned in the Light chain expression vector (VL mR007) encoding also for human Kappa region (FIG. 17) and in the Heavy chain expression vectors (VH mR007) encoding also for a native Fc region named Fc0 (FIG. 18). Transient transfection on CHO dhfr$^{-/-}$ cells by lipofection was performed.

Construction of antibody variants: Substitutions in the Fc domain as described in Table 4 were introduced using "megaprimer" method of site-directed mutagenesis (Sarkar et al., 1990). Positions are numbered according to the Kabat index (Identical V region amino acid sequences and segments of sequences in antibodies of different specificities). Relative contributions of VH and VL genes, minigenes, and complementarity-determining regions to binding of antibody-combining sites were analyzed (Kabat et al., 1991). Then sequences were then cloned in the Light chain expression vector (VL mR007) and in the Heavy MAb expression vectors (VH mR007) encoding different Fc variants (See Table 4).

Transient transfection on CHO dhfr$^{-/-}$ cells by lipofection was performedHeavy and light chain constructs were co-transfected into CHO DG44 (ATCC) suitable for MAb screening. Antibodies were purified using protein A affinity chromatography (GE Healthcare).

We constructed several variants including one or more substitution variants according to Table 4, to enhance ability to mediate effector function. For example:

Fc24 SEQ ID NO: 32
Fc34 SEQ ID NO: 34
Fc40 SEQ ID NO: 36

Mab Expression.

The empty CHO dhfr−/− cells (purchased by the ATCC collection) were co-transfected with the pcDNA3.3 expression vector for light chain and with the pcDNA3.3 expression vector for heavy chain following transient transfection procedure established in our laboratory. General characteristics of this MAb expression vector are shown in EP 2 595 662 and U.S. Pat. No. 9,663,583. The empty CHO cells were co-transfected with the pcDNA3.3–expression vector for light chain (Invitrogen) and with the pcDNA3.3 expression vector for heavy chain (Invitrogen) following transient transfection procedure established in our laboratory. General characteristics of this research MAb expression vector are shown in EP 2 595 662 and U.S. Pat. No. 9,663,583 (FIG. 27 and Mab expression in the Part Example of these prior patents) which are incorporated herein by reference. By using the pcDNA3.3 vector, expression of these chimeric antibody chains in mammalian cells was controlled by the full-length human CMV immediate early promoter/enhancer. Secretion of H and L chains were enabled by the respective human IgH leader sequence. And in the 3' region, a Herpes Simplex Virus thymidine kinase polyA tail allows for efficient induction and stabilization of mRNA. The coding regions for light and heavy chains of anti-CD5 MAb are introduced into the expression vector pcDNA3.3-TOPO in the TOPO cloning site. The transformants are analyzed for correct orientation and reading frame, the expression vector may be transfected into CHO cell line Comparative Characterization of Complement Dependent Cytotoxicity Activity (CDC) Between the Native Fc0 Versus Optimized Fc Variants.

Figure 2:
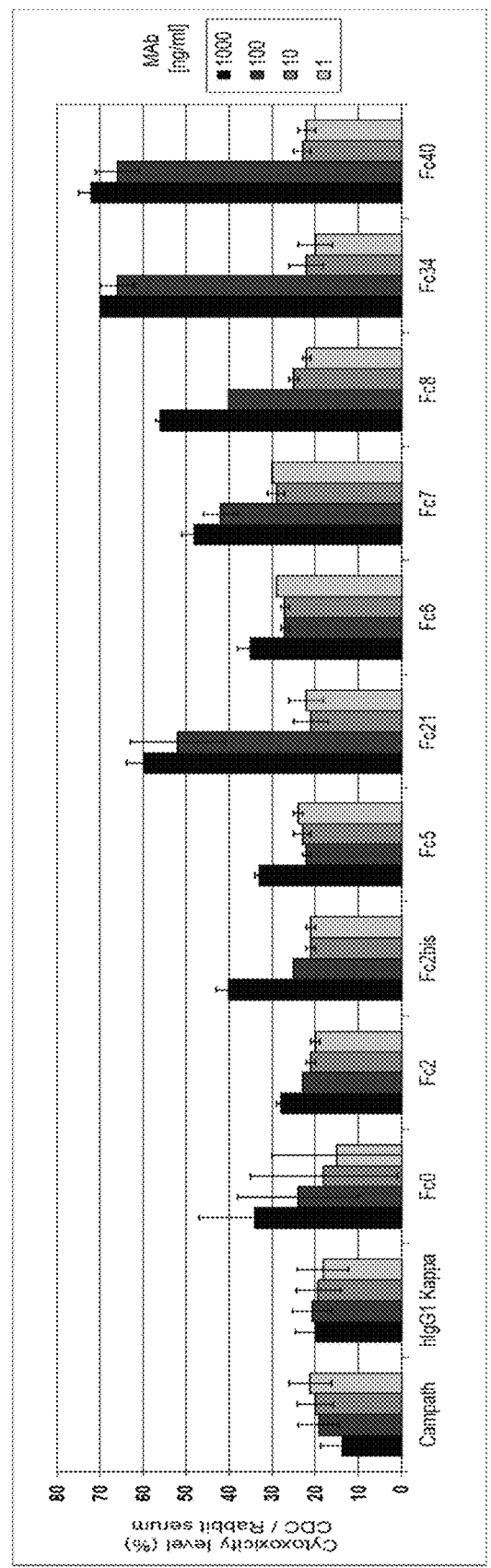
FIGS. 2, 3 and 4: Investigation and comparison on chR007 Fc variants to enhance CDC triggered cytotoxicity on Cem cell line, (Mean+/−SD, N=2).
Figure 3:
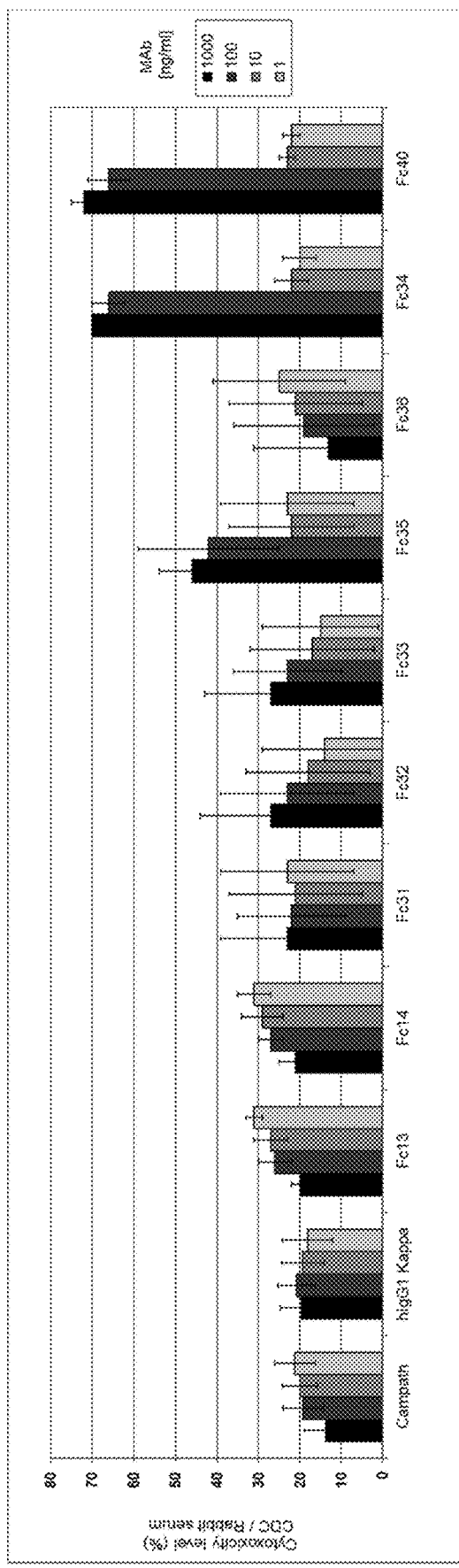
Figure 4:
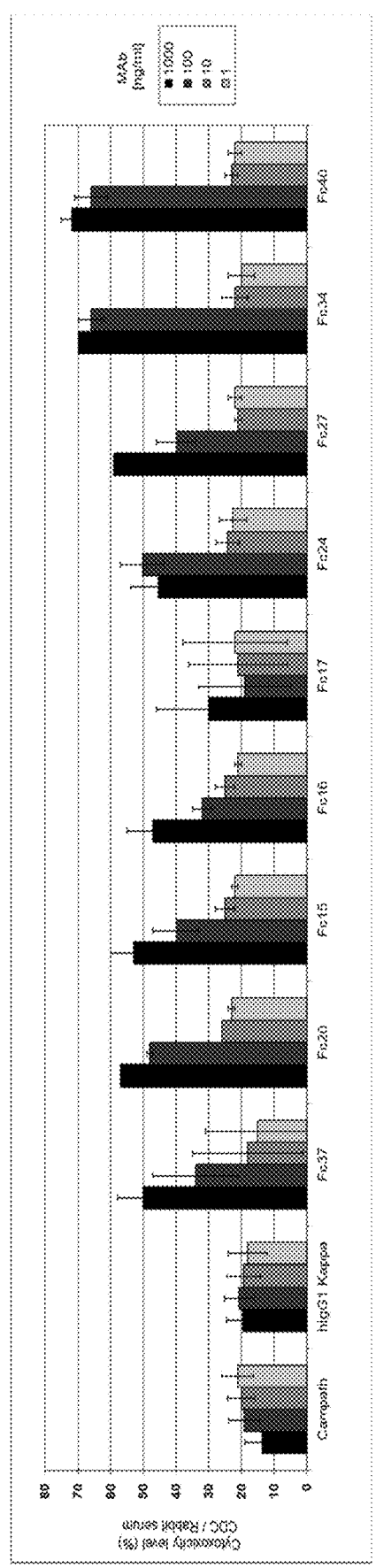

In many applications, chimeric antibodies have demonstrated improved effector function in complement-mediated tumor cells lysis and in antibody-dependent cellular cytotoxicity assays as compared to the parental murine monoclonal antibody (Liu et al., 1987; Nishimura et al., 1987; Hamada et al., 1990). The native chimeric MAb chR007 Fc0 induced modest CDC against T leukemia Cem cell line, whereas the same chR007 Mab having some variant Fc (Fc24, Fc34 and Fc40) exhibited a higher cell cytotoxicity: these MAbs are named chR007 Fc24, chR007 Fc34 and chR007 Fc40 (FIGS. 2, 3, 4).

Figure 5:
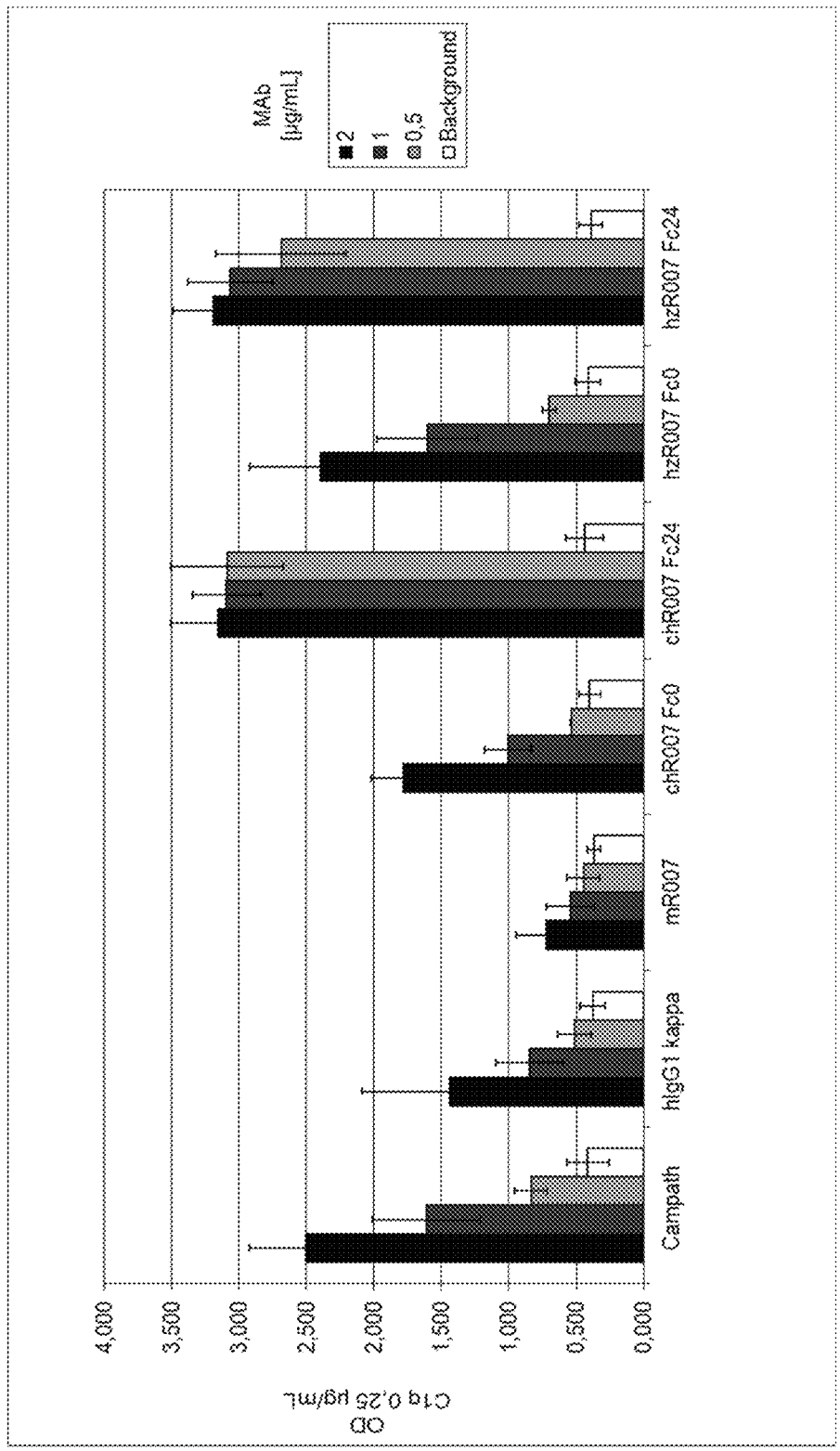
FIG. 5: Investigation on C1q binding from murine, chimeric to humanized Hz116 MAb with or without Fc optimisation, (Mean+/−SD, N=2).

As shown in FIG. 5, the chimeric chR007 Fc24 and the humanized 7Hz116 Fc24 bound the C1q complement with a higher efficacy compared to chR007 Fc0.

Figure 6:
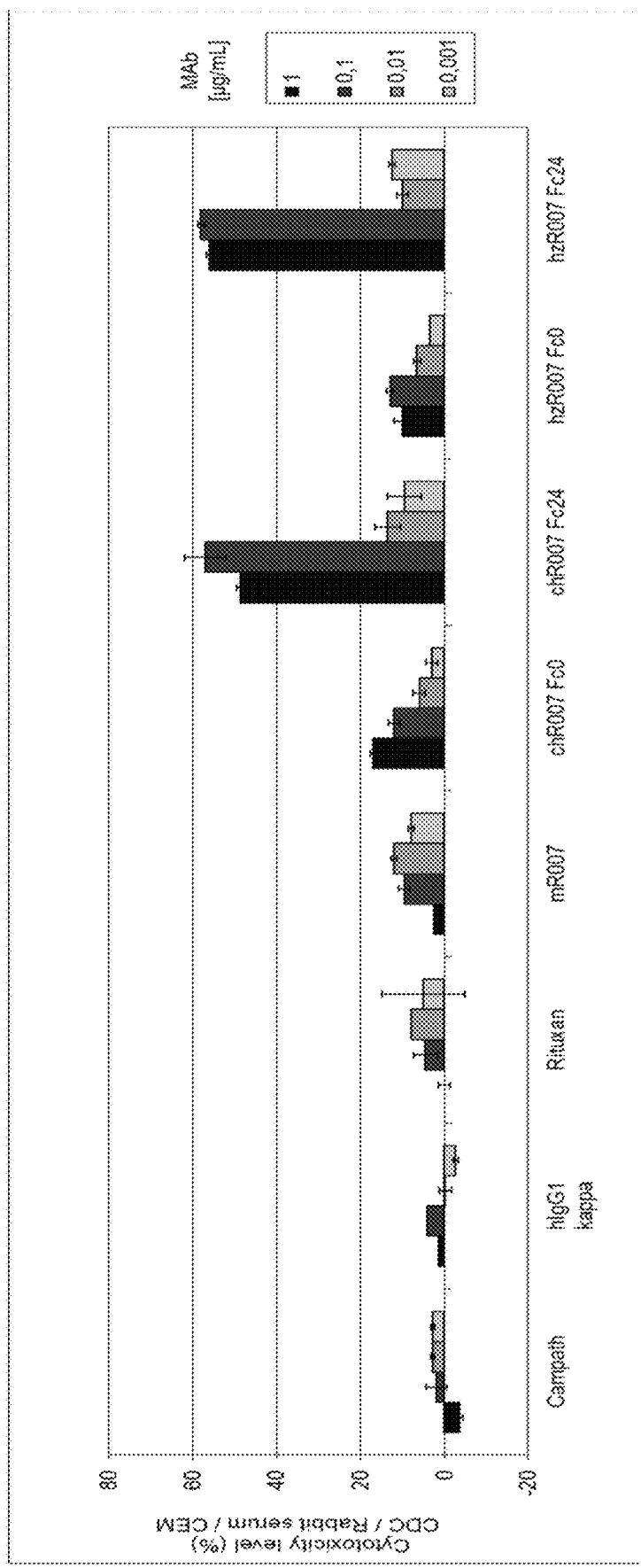
FIG. 6: Investigation on CDC triggered activity on T leukemia CEM cell with murine, chimeric, or humanized Hz116 MAb with or without Fc optimisation, (Mean+/−SD, N=2).
Figure 7:
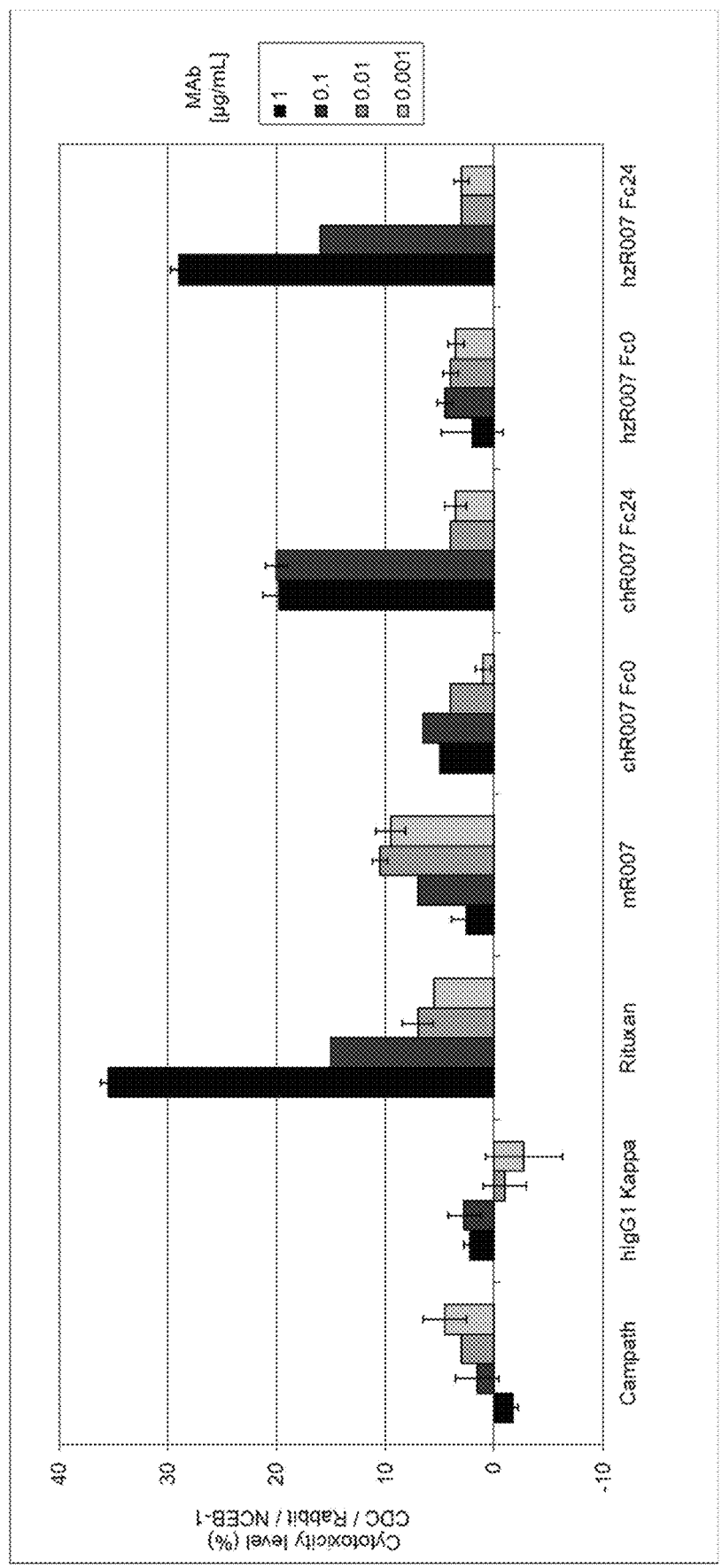
FIG. 7: Investigation on CDC triggered activity on Mantle lymphoma NCEB-1 cells with murine, chimeric, or humanized Hz116 MAb with or without Fc optimisation, (Mean+/−SD, N=2).

In the presence of rabbit serum containing natural complement, the variants chR007 Fc24 and hzR007 116 Fc24 triggered a higher level of CDC compared with Fc0 derivate MAb anti CD5, for T leukaemia cells (FIG. 6) or for Mantle lymphoma NCEB-1 cells (FIG. 7).

Comparative Characterization of Antibody Dependent Cytotoxicity Activity (ADCC) Between the Chimeric and Humanized Antibodies Comprising a Native Fc0 Versus Optimized Fc Variants.

Figure 8:
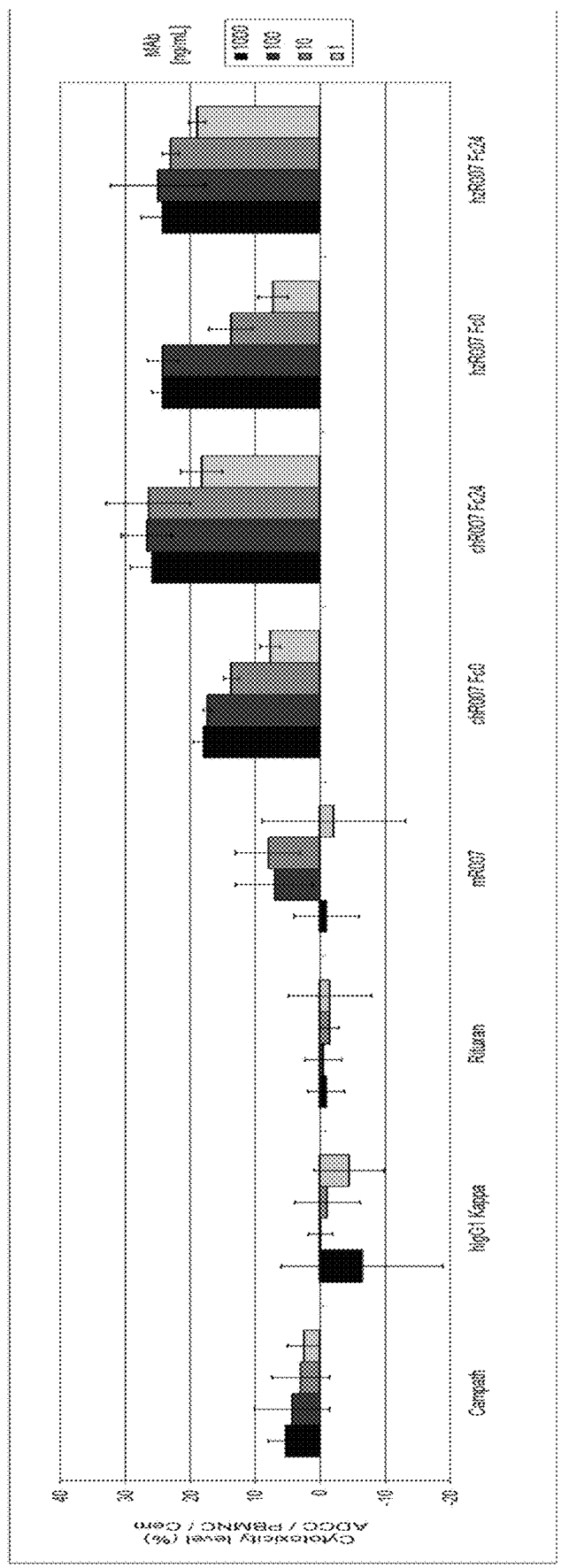
FIG. 8: Investigation on ADCC triggered activity on T leukemia CEM cell with murine, chimeric, or humanized Hz116 MAb with or without Fc optimisation, (Mean+/−SD, N=4).

The MAb activity to mediate ADCC from the MAb variant panel was measured using Cem target cells firstly in isolated peripheral blood mononuclear cells-based assays (FIG. 8). The potency and efficacy of the chR007 Fc24 and HzR007 116 Fc24 was notably higher when compared to the respective chR007 Fc0 and HzR007 116 Fc0.

Figure 9:
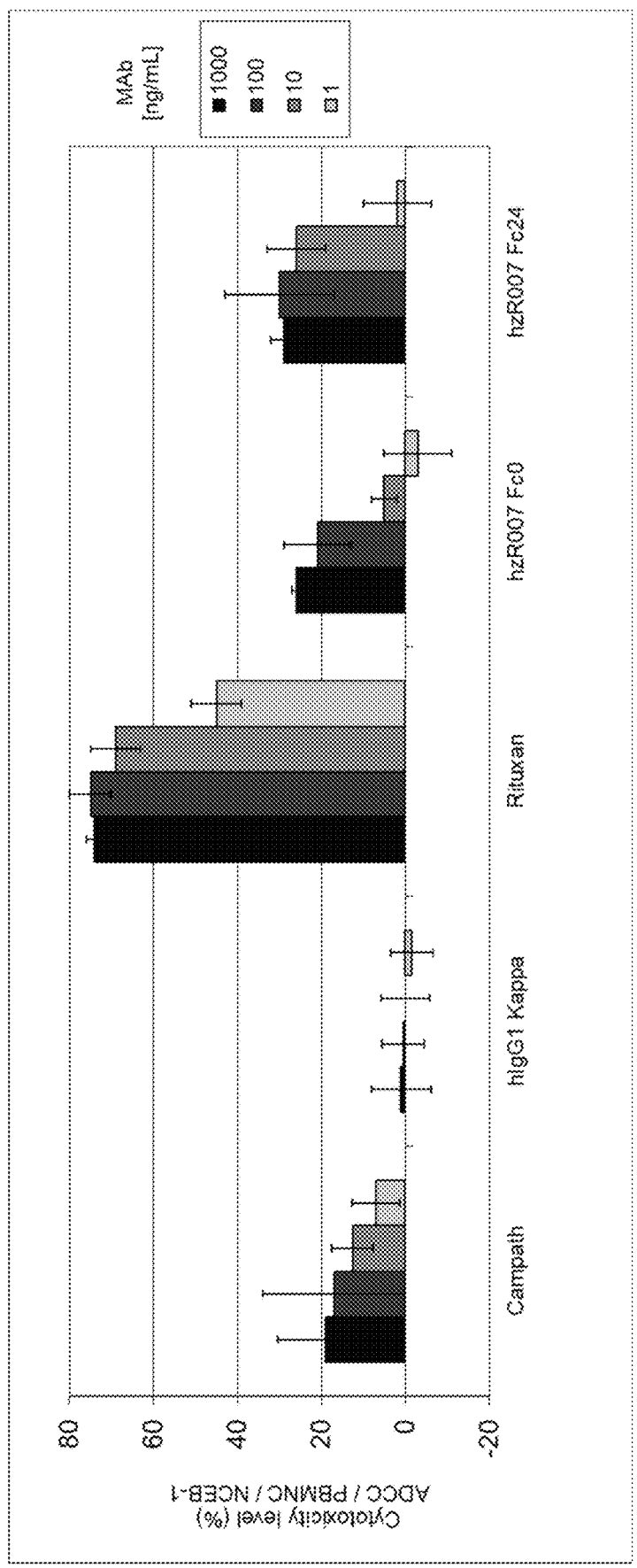
FIG. 9: Investigation on ADCC triggered activity on Mantle lymphoma NCEB-1 cells with humanized Hz116 MAb with or without Fc optimisation, (Representative experiment)

The activity was also assessed by using Mantle Lymphoma NCBE-1 cells. The chimeric chR007 Fc24 and the humanized HzR007 116 Fc24 antibody efficiently triggered ADCC (FIG. 9).

In Vivo Inhibition of Tumor Growth of T Leukemia or Mantle Lymphoma

Figure 10:
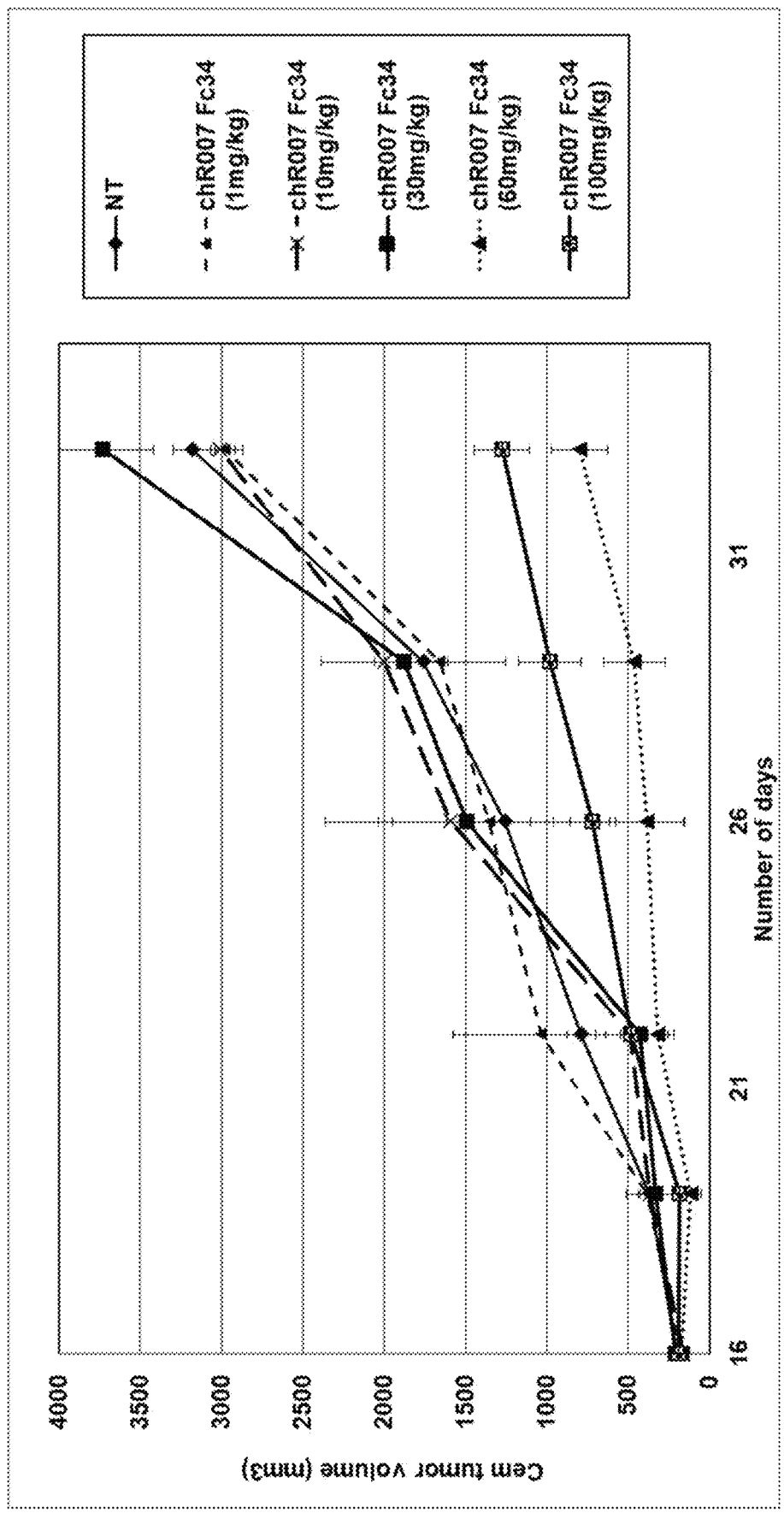
FIG. 10: Inhibition of in vivo tumor growth on T leukemia Cem cells in the presence of the chimeric R007 Fc34 (chR007 Fc34).
Figure 11:
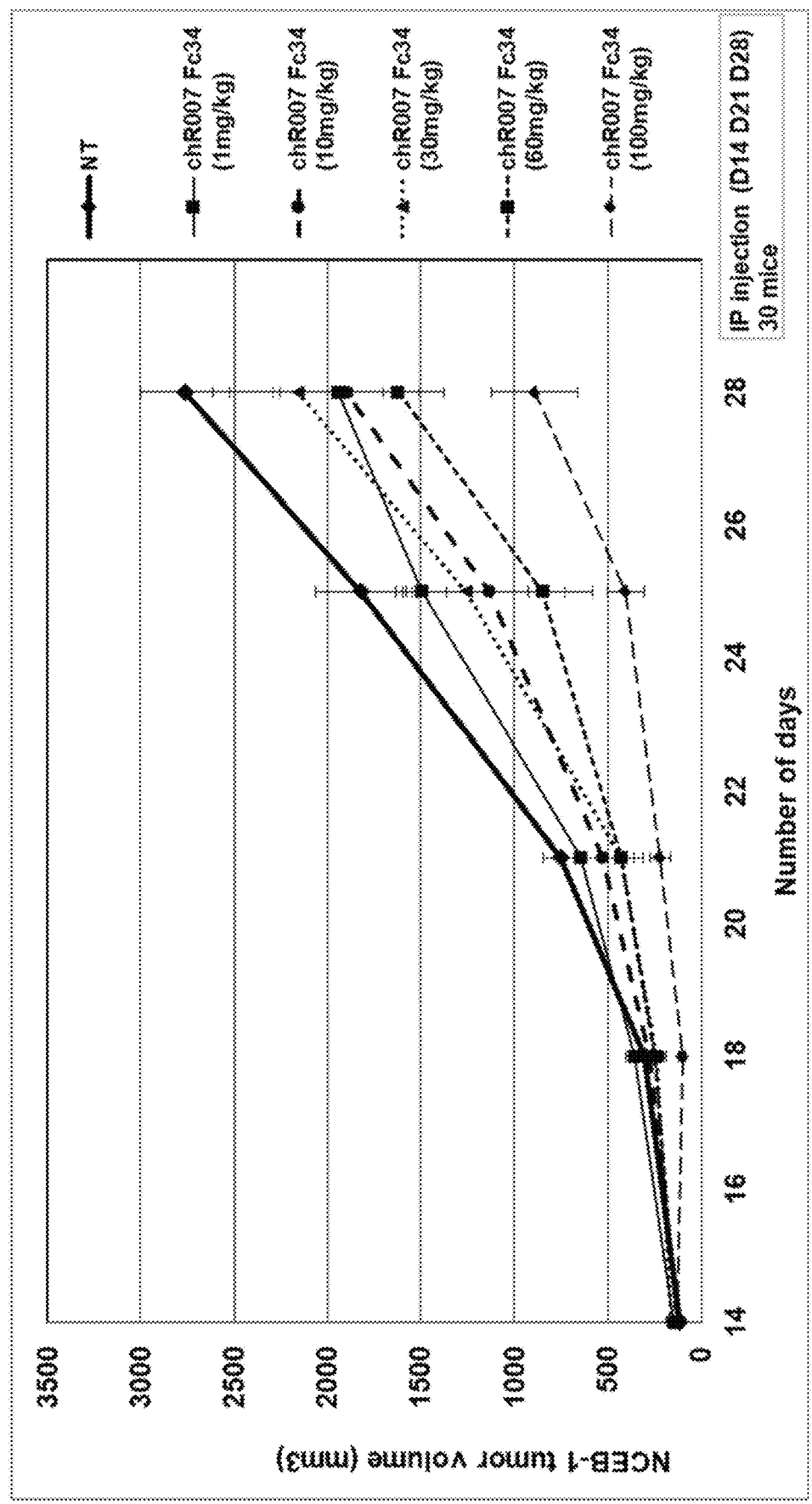
FIG. 11: Inhibition of in vivo tumor growth on Mantle lymphoma NCEB-1 cells in the presence of the chimeric R007 Fc34 (chR007 Fc34).

Results show in FIG. 10 and in FIG. 11 revealed that T leukemia (Cem cell line) and Mantle lymphoma (NCBE-1) was reduced following the dose-dependent manner in the presence of the chimeric Mab R007 FC34.

The invention claimed is:

1. A pharmaceutical composition comprising a monoclonal antibody, or an antigen-binding fragment thereof, said antibody or fragment thereof specifically binding to CD5, wherein said antibody or fragment comprises a VL chain and a VH chain of the murine monoclonal antibody mR007, and wherein said VL and VH chains are selected from the group consisting of:

(1) a VL chain comprising the following three CDRs: a L-CDR1 comprising sequence SEQ ID NO: 1, a L-CDR2 comprising sequence RAS, a L-CDR3 comprising sequence SEQ ID NO: 2; and a VH chain comprising the following three CDRs: a H-CDR1 comprising sequence SEQ ID NO: 3, a H-CDR2 comprising sequence SEQ ID NO: 4, a H-CDR3 comprising sequence SEQ ID NO: 5;

(2) a VL chain comprising the following three CDRs: a L-CDR1 comprising sequence SEQ ID NO: 6, a L-CDR2 comprising sequence SEQ ID NO: 7, a L-CDR3 comprising sequence SEQ ID NO: 2; and a VH chain comprising the following three CDRs: a H-CDR1 comprising sequence SEQ ID NO: 8, a H-CDR2 comprising sequence SEQ ID NO: 9, a H-CDR3 comprising sequence SEQ ID NO: 10; and (3) a VL chain comprising the following three CDRs: a L-CDR1 comprising sequence SEQ ID NO: 1, a L-CDR2 comprising sequence RAS, a L-CDR3 comprising sequence SEQ ID NO: 2; and a VH chain comprising the following three CDRs: a H-CDR1 comprising sequence SEQ ID NO: 11, a H-CDR2 comprising sequence SEQ ID NO: 4, a H-CDR3 comprising sequence SEQ ID NO: 10, and a pharmaceutically acceptable vehicle or excipient.

2. The composition according to claim 1, wherein said monoclonal antibody, or antigen-binding fragment thereof, comprises a VL region comprising sequence SEQ ID NO: 18, a VH region comprising sequence SEQ ID NO: 20, and a human IgG1 Fc region.

3. The composition according to claim 1, wherein the monoclonal antibody, or antigen-binding fragment thereof, is humanized.

4. The composition according to claim 1, wherein the monoclonal antibody comprises an Fc region comprising sequence SEQ ID NO: 28, 32, 34 or 36.

5. A monoclonal antibody, or an antigen-binding fragment thereof, said antibody or fragment thereof specifically binding to CD5 and comprising (1a) a VL chain comprising the following three CDRs: a L-CDR1 comprising sequence SEQ ID NO: 12, a L-CDR2 comprising sequence RAS, a L-CDR3 comprising sequence SEQ ID NO: 2; and a VH chain comprising the following three CDRs: a H-CDR1 comprising sequence SEQ ID NO: 3, a H-CDR2 comprising sequence SEQ ID NO: 13, a H-CDR3 comprising sequence SEQ ID NO: 5;

(2a) a VL chain comprising the following three CDRs: a L-CDR1 comprising sequence SEQ ID NO: 14, a L-CDR2 comprising sequence SEQ ID NO: 7, a L-CDR3 comprising sequence SEQ ID NO: 2; and a VH chain comprising the following three CDRs: a H-CDR1 comprising sequence SEQ ID NO: 8, a H-CDR2 comprising sequence SEQ ID NO: 15, a H-CDR3 comprising sequence SEQ ID NO: 10; or (3a) a VL chain comprising the following three CDRs: a L-CDR1 comprising sequence SEQ ID NO: 12, a L-CDR2 comprising sequence RAS, a L-CDR3 comprising sequence SEQ ID NO: 2; and a VH chain comprising the following three CDRs: a H-CDR1 comprising sequence SEQ ID NO: 11, a H-CDR2 comprising sequence SEQ ID NO: 13, a H-CDR3 comprising sequence SEQ ID NO: 10.

6. The monoclonal antibody or antigen-binding fragment thereof, according to claim 5, which comprises a VL comprising SEQ ID NO: 22 and a VH comprising SEQ ID NO: 24.

7. The monoclonal antibody according to claim 5, comprising an Fc region comprising sequence SEQ ID NO: 28, 32, 34 or 36.

8. A monoclonal antibody, or an antigen-binding fragment thereof, said antibody or fragment thereof specifically binding to CD5 and comprising (1b) VL chain comprising the following three CDRs: a L-CDR1 comprising sequence SEQ ID NO: 12, a L-CDR2 comprising sequence RAS, a L-CDR3 comprising sequence SEQ ID NO: 2; and a VH chain comprising the following three CDRs: a H-CDR1 comprising sequence SEQ ID NO: 3, a H-CDR2 comprising sequence SEQ ID NO: 16, a H-CDR3 comprising sequence SEQ ID NO: 5;

(2b) a VL chain comprising the following three CDRs: a L-CDR1 comprising sequence SEQ ID NO: 14, a L-CDR2 comprising sequence SEQ ID NO: 7, a L-CDR3 comprising sequence SEQ ID NO: 2; and a VH chain comprising the following three CDRs: a H-CDR1 comprising sequence SEQ ID NO: 8, a H-CDR2 comprising sequence SEQ ID NO: 17, a H-CDR3 comprising sequence SEQ ID NO: 10; or (3b) a VL chain comprising the following three CDRs: a L-CDR1 comprising sequence SEQ ID NO: 12, a L-CDR2 comprising sequence RAS, a L-CDR3 comprising sequence SEQ ID NO: 2; and a VH chain comprising the following three CDRs: a H-CDR1 comprising sequence SEQ ID NO: 11, a H-CDR2 comprising sequence SEQ ID NO: 16, a H-CDR3 comprising sequence SEQ ID NO: 10.

9. The monoclonal antibody or antigen-binding fragment thereof, according to claim 7, which comprises a VL comprising SEQ ID NO: 22 and a VH comprising SEQ ID NO: 26.

10. The monoclonal antibody according to claim 8, comprising an Fc region comprising sequence SEQ ID NO: 28, 32, 34 or 36.

11. A method for treating a CD5 positive cancer in a patient in need thereof, comprising administering to said patient an effective amount of a pharmaceutical composition according to claim 1.

12. The method according to claim 11, wherein the CD5 positive cancer is T leukemia or Mantle cell lymphoma.

13. A method for treating a CD5 positive cancer in a patient in need thereof, comprising administering to said patient an effective amount of a monoclonal antibody, or an antigen-binding fragment thereof, according to claim 5.

14. The method according to claim 13, wherein the CD5 positive cancer is T leukemia or Mantle cell lymphoma.

15. A method for treating a CD5 positive cancer in a patient in need thereof, comprising administering to said patient an effective amount of a monoclonal antibody, or an antigen-binding fragment thereof, according to claim 8.

16. The method according to claim 15, wherein the CD5 positive cancer is T leukemia or Mantle cell lymphoma.

* * * * *

SEQUENCE LISTING

```
<160> NUMBER OF SEQ ID NOS: 37

<210> SEQ ID NO 1
<211> LENGTH: 10
<212> TYPE: PRT
<213> ORGANISM: artificial sequence
<220> FEATURE:
<223> OTHER INFORMATION: L-CDR1 mR007

<400> SEQUENCE: 1

Glu Ser Val Asp Asn Tyr Gly Ser Ser Ser
1               5                   10

<210> SEQ ID NO 2
<211> LENGTH: 10
<212> TYPE: PRT
<213> ORGANISM: artificial sequence
<220> FEATURE:
<223> OTHER INFORMATION: L-CDR3 mR007

<400> SEQUENCE: 2

Gln Gln Ser Asn Glu Asp Leu Pro Tyr Thr
1               5                   10

<210> SEQ ID NO 3
<211> LENGTH: 8
<212> TYPE: PRT
<213> ORGANISM: artificial sequence
<220> FEATURE:
<223> OTHER INFORMATION: H-CDR1 mR007

<400> SEQUENCE: 3

Gly Phe Thr Phe Ser Asn Tyr Trp
1               5

<210> SEQ ID NO 4
<211> LENGTH: 10
<212> TYPE: PRT
<213> ORGANISM: artificial sequence
<220> FEATURE:
```

<223> OTHER INFORMATION: H-CDR2 mR007

<400> SEQUENCE: 4

Ile Arg Leu Lys Ser Asn Asn Tyr Ala Thr
1               5                   10

<210> SEQ ID NO 5
<211> LENGTH: 8
<212> TYPE: PRT
<213> ORGANISM: artificial sequence
<220> FEATURE:
<223> OTHER INFORMATION: H-CDR3 mR007

<400> SEQUENCE: 5

Thr Arg Asp Trp Glu Phe Ala Tyr
1               5

<210> SEQ ID NO 6
<211> LENGTH: 15
<212> TYPE: PRT
<213> ORGANISM: artificial sequence
<220> FEATURE:
<223> OTHER INFORMATION: L-CDR1 mR007

<400> SEQUENCE: 6

Arg Thr Ser Glu Ser Val Asp Asn Tyr Gly Ser Ser Ser Met Asn
1               5                   10                  15

<210> SEQ ID NO 7
<211> LENGTH: 7
<212> TYPE: PRT
<213> ORGANISM: artificial sequence
<220> FEATURE:
<223> OTHER INFORMATION: L-CDR2 mR007

<400> SEQUENCE: 7

Arg Ala Ser Asn Leu Asp Ser
1               5

<210> SEQ ID NO 8
<211> LENGTH: 5
<212> TYPE: PRT
<213> ORGANISM: artificial sequence
<220> FEATURE:
<223> OTHER INFORMATION: H-CDR1 mR007

<400> SEQUENCE: 8

Asn Tyr Trp Met Asn
1               5

<210> SEQ ID NO 9
<211> LENGTH: 19
<212> TYPE: PRT
<213> ORGANISM: artificial sequence
<220> FEATURE:
<223> OTHER INFORMATION: H-CDR2 mR007

<400> SEQUENCE: 9

Glu Ile Arg Leu Lys Ser Asn Asn Tyr Ala Thr His Tyr Ala Glu Ser
1               5                   10                  15

Val Lys Gly

<210> SEQ ID NO 10
<211> LENGTH: 6
<212> TYPE: PRT
<213> ORGANISM: artificial sequence

```
<220> FEATURE:
<223> OTHER INFORMATION: H-CDR3 mR007

<400> SEQUENCE: 10

Asp Trp Glu Phe Ala Tyr
1               5

<210> SEQ ID NO 11
<211> LENGTH: 4
<212> TYPE: PRT
<213> ORGANISM: artificial sequence
<220> FEATURE:
<223> OTHER INFORMATION: H-CDR1 mR007

<400> SEQUENCE: 11

Ser Asn Tyr Trp
1

<210> SEQ ID NO 12
<211> LENGTH: 10
<212> TYPE: PRT
<213> ORGANISM: artificial sequence
<220> FEATURE:
<223> OTHER INFORMATION: L-CDR1 Hz

<400> SEQUENCE: 12

Gln Ser Val Asp Asn Tyr Gly Ser Ser Ser
1               5                   10

<210> SEQ ID NO 13
<211> LENGTH: 10
<212> TYPE: PRT
<213> ORGANISM: artificial sequence
<220> FEATURE:
<223> OTHER INFORMATION: H-CDR2 Hz

<400> SEQUENCE: 13

Ile Arg Ser Lys Ala Asn Ser Tyr Ala Thr
1               5                   10

<210> SEQ ID NO 14
<211> LENGTH: 15
<212> TYPE: PRT
<213> ORGANISM: artificial sequence
<220> FEATURE:
<223> OTHER INFORMATION: L-CDR1 Hz

<400> SEQUENCE: 14

Lys Ser Ser Gln Ser Val Asp Asn Tyr Gly Ser Ser Ser Leu Ala
1               5                   10                  15

<210> SEQ ID NO 15
<211> LENGTH: 11
<212> TYPE: PRT
<213> ORGANISM: artificial sequence
<220> FEATURE:
<223> OTHER INFORMATION: H-CDR2 Hz

<400> SEQUENCE: 15

Glu Ile Arg Ser Lys Ala Asn Ser Tyr Ala Thr
1               5                   10

<210> SEQ ID NO 16
<211> LENGTH: 10
<212> TYPE: PRT
<213> ORGANISM: artificial sequence
<220> FEATURE:
```

<223> OTHER INFORMATION: H-CDR2 Hz

<400> SEQUENCE: 16

Ile Arg Leu Lys Ala Asn Asn Tyr Ala Thr
1               5                   10

<210> SEQ ID NO 17
<211> LENGTH: 19
<212> TYPE: PRT
<213> ORGANISM: artificial sequence
<220> FEATURE:
<223> OTHER INFORMATION: H-CDR2 Hz

<400> SEQUENCE: 17

Arg Ile Arg Leu Lys Ala Asn Asn Tyr Ala Thr Ala Tyr Ala Ala Ser
1               5                   10                  15

Val Lys Gly

<210> SEQ ID NO 18
<211> LENGTH: 131
<212> TYPE: PRT
<213> ORGANISM: artificial sequence
<220> FEATURE:
<223> OTHER INFORMATION: mVL aas

<400> SEQUENCE: 18

Met Gly Trp Ser Cys Ile Ile Leu Phe Leu Val Ala Thr Ala Thr Gly
1               5                   10                  15

Val His Ser Asp Ile Val Leu Thr Gln Ser Pro Ala Ser Leu Ala Val
                20                  25                  30

Ser Leu Gly Gln Arg Ala Thr Ile Ser Cys Arg Thr Ser Glu Ser Val
            35                  40                  45

Asp Asn Tyr Gly Ser Ser Ser Met Asn Trp Phe Gln Gln Lys Pro Gly
        50                  55                  60

Gln Pro Pro Lys Leu Leu Ile Tyr Arg Ala Ser Asn Leu Asp Ser Gly
65                  70                  75                  80

Ile Pro Ala Arg Phe Ser Gly Ser Gly Ser Arg Ser Asp Phe Thr Leu
                85                  90                  95

Thr Ile Asn Pro Val Glu Ala Asp Asp Val Ala Thr Tyr Tyr Cys Gln
                100                 105                 110

Gln Ser Asn Glu Asp Leu Pro Tyr Thr Phe Gly Gly Gly Thr Lys Leu
            115                 120                 125

Glu Ile Lys
        130

<210> SEQ ID NO 19
<211> LENGTH: 393
<212> TYPE: DNA
<213> ORGANISM: artificial sequence
<220> FEATURE:
<223> OTHER INFORMATION: mVL

<400> SEQUENCE: 19
atgggatgga gctgtatcat cctcttcttg gtagcaacag ctacaggcgt gcactccgac      60
attgtactga cccagtctcc agcctctttg gctgtgtctc tagggcagag ggccaccata     120
tcctgcagaa ccagtgaaag tgttgataat tatggcagta gttctatgaa ctggttccag     180
cagaaaccag gacagccacc caaactcctc atctaccgtg catccaacct agattctggg     240
atccctgcca ggttcagtgg cagtgggtct aggtcagact tcaccctcac cattaatcct     300

```
gtggaggctg atgatgttgc aacctattac tgtcagcaaa gtaacgagga tcttccgtac    360
acgtttggag ggggaaccaa gctcgagatc aaa                                 393
```

<210> SEQ ID NO 20
<211> LENGTH: 117
<212> TYPE: PRT
<213> ORGANISM: artificial sequence
<220> FEATURE:
<223> OTHER INFORMATION: mVH

<400> SEQUENCE: 20

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Arg Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Asp Trp Glu Phe Ala Tyr Trp Gly Gln Gly Thr Leu
            100                 105                 110

Val Thr Val Ser Ser
        115

<210> SEQ ID NO 21
<211> LENGTH: 351
<212> TYPE: DNA
<213> ORGANISM: artificial sequence
<220> FEATURE:
<223> OTHER INFORMATION: mVH

<400> SEQUENCE: 21

```
gaggtgaagc ttgaggagtc tggagggggc ttggtgcaac ctggaggatc catgaaactc    60
tcctgtgttg cctctggatt cactttcagt aactactgga tgaactgggt ccgccagtct   120
ccagagaagg ggcttgaatg ggttgctgaa attagattga aatctaataa ttatgcaaca   180
cattatgcgg agtctgtgaa agggaggttc accatctcaa gagatgattc agaagtagt    240 gtctacctgc aaatgaacaa cttaagagct gaagacactg gcatttatta ctgtaccagg   300
gactgggagt ttgcttactg gggccaaggg actctggtca ccgtctcctc a            351
```

<210> SEQ ID NO 22
<211> LENGTH: 112
<212> TYPE: PRT
<213> ORGANISM: artificial sequence
<220> FEATURE:
<223> OTHER INFORMATION: Humanized VL

<400> SEQUENCE: 22

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Asp Asn Tyr
            20                  25                  30

Gly Ser Ser Ser Leu Ala Trp Tyr Gln Gln Lys Pro Gly Gln Pro Pro
        35                  40                  45

```
Lys Leu Leu Ile Tyr Arg Ala Ser Asn Leu Asp Ser Gly Val Pro Asp
    50                  55                  60

Arg Phe Ser Gly Ser Gly Ser Gly Thr Asp Phe Thr Leu Thr Ile Ser
 65                  70                  75                  80

Ser Val Gln Ala Glu Asp Val Ala Val Tyr Tyr Cys Gln Gln Ser Asn
                 85                  90                  95

Glu Asp Leu Pro Tyr Thr Phe Gly Gln Gly Thr Lys Leu Glu Ile Lys
            100                 105                 110
```

<210> SEQ ID NO 23
<211> LENGTH: 336
<212> TYPE: DNA
<213> ORGANISM: artificial sequence
<220> FEATURE:
<223> OTHER INFORMATION: VL humanized

<400> SEQUENCE: 23

```
gatattgtca tgactcagtc acctgattcc ttggctgttt ctctcggcga acgagctacc    60
atcaactgta agagttccca gagtgtagac aattacggca gctcaagtct cgcttggtac   120
cagcagaagc ctgggcagcc tcccaaactg ttgatatata gggcaagtaa cctggactcc   180
ggcgtgccag accgattcag tggtagcggc tccggtactg atttcaccct gaccatctcc   240
tccgtgcagg ctgaggatgt ggcagtatat tactgtcagc aatctaatga agatttgccc   300
tacacctttg gacagggcac taaactggag atcaag                             336
```

<210> SEQ ID NO 24
<211> LENGTH: 117
<212> TYPE: PRT
<213> ORGANISM: artificial sequence
<220> FEATURE:
<223> OTHER INFORMATION: VH Hz116

<400> SEQUENCE: 24

```
Glu Val Gln Leu Val Glu Ser Gly Gly Gly Leu Val Gln Pro Gly Gly
  1               5                  10                  15

Ser Leu Lys Leu Ser Cys Ala Ala Ser Gly Phe Thr Phe Ser Asn Tyr
             20                  25                  30

Trp Met His Trp Val Arg Gln Ala Ser Gly Lys Gly Leu Glu Trp Val
         35                  40                  45

Ala Glu Ile Arg Ser Lys Ala Asn Ser Tyr Ala Thr Ala Tyr Ala Ala
     50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Arg Asp Trp Glu Phe Ala Tyr Trp Gly Gln Gly Thr Leu
            100                 105                 110

Val Thr Val Ser Ser
        115
```

<210> SEQ ID NO 25
<211> LENGTH: 351
<212> TYPE: DNA
<213> ORGANISM: artificial sequence
<220> FEATURE:
<223> OTHER INFORMATION: VH Hz116

<400> SEQUENCE: 25

```
gaagttcagc ttgttgaaag tggaggtggt ttggtacagc caggtggaag cctcaaactc    60
```

```
agttgcgccg cctctggttt taccttctca aactactgga tgcactgggt tcgccaggcc   120
agcgggaagg ggcttgaatg ggtggcagaa ataaggtcca aggccaacag ttacgctaca   180
gcttatgccg cttcagtcaa aggtcggttc actatctccc gtgacgacag taagaatact   240
gcttacctgc agatgaatag tctgaaaaca gaggacactg ccgtgtatta ctgcacacgc   300
gattgggaat cgcatactg ggggcaggga acactggtca ctgtgagtag t            351
```

```
<210> SEQ ID NO 26
<211> LENGTH: 117
<212> TYPE: PRT
<213> ORGANISM: artificial sequence
<220> FEATURE:
<223> OTHER INFORMATION: VH Hz118

<400> SEQUENCE: 26
```

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Trp Met Asn Trp Val Arg Gln Ala Ser Gly Lys Gly Leu Glu Trp Val
        35                  40                  45

Gly Arg Ile Arg Leu Lys Ala Asn Asn Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Asp Trp Glu Phe Ala Tyr Trp Gly Gln Gly Thr Leu
            100                 105                 110

Val Thr Val Ser Ser
        115
```

```
<210> SEQ ID NO 27
<211> LENGTH: 351
<212> TYPE: DNA
<213> ORGANISM: artificial sequence
<220> FEATURE:
<223> OTHER INFORMATION: VH Hz118

<400> SEQUENCE: 27
gaagttcagc ttgttgaaag tggaggtggt ttggtacagc caggtggaag cctcaaactc    60
agttgcgccg cctctggttt taccttctca aactactgga tgaactgggt tcgccaggcc   120
agcgggaagg ggcttgaatg ggtgggaaga ataaggctca aggccaacaa ttacgctaca   180
gcttatgccg cttcagtcaa aggtcggttc actatctccc gtgacgacag taagaatact   240
gcttacctgc agatgaatag tctgaaaaca gaggacactg ccgtgtatta ctgcacacgc   300
gattgggaat cgcatactg ggggcaggga acactggtca ctgtgagtag t             351
```

```
<210> SEQ ID NO 28
<211> LENGTH: 330
<212> TYPE: PRT
<213> ORGANISM: Homo sapiens

<400> SEQUENCE: 28
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
```

```
                    20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                 70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 29
<211> LENGTH: 990
<212> TYPE: DNA
<213> ORGANISM: Homo sapiens

<400> SEQUENCE: 29
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag cgccctgac cagcggcgtg cacaccttcc cggctgtcct acagtcctca     180
ggactctact ccctcagcag cgtcgtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
```

```
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                    990
```

<210> SEQ ID NO 30
<211> LENGTH: 107
<212> TYPE: PRT
<213> ORGANISM: Homo sapiens

<400> SEQUENCE: 30

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 31
<211> LENGTH: 321
<212> TYPE: DNA
<213> ORGANISM: Homo sapiens

<400> SEQUENCE: 31

```
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg t                                             321
```

<210> SEQ ID NO 32
<211> LENGTH: 330
<212> TYPE: PRT
<213> ORGANISM: Artificial sequence
<220> FEATURE:
<223> OTHER INFORMATION: Fc24

<400> SEQUENCE: 32

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Leu Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Pro Glu
                165                 170                 175
Glu Gln Tyr Asn Ser Thr Leu Arg Val Val Ser Leu Leu Thr Val Leu
            180                 185                 190
His Gln Asp Trp Leu Asn Gly Lys Glu Tyr Lys Cys Lys Val Ser Asn
        195                 200                 205
Ala Ala Leu Pro Ala Pro Ile Ala Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Leu Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 33
<211> LENGTH: 990
<212> TYPE: DNA
<213> ORGANISM: Artificial sequence
<220> FEATURE:
<223> OTHER INFORMATION: Fc24

<400> SEQUENCE: 33
gcctccacca agggcccatc ggtcttcccc ctggcaccct cctccaagag cacctctggg     60
ggcacagcgg ccctgggctg cctggtcaag gactacttcc ccgaaccggt gacggtgtcg    120

-continued

```
tggaactcag gcgccctgac cagcggcgtg cacaccttcc cggctgtcct acagtcctca      180
ggactctact ccctcagcag cgtcgtgacc gtgccctcca gcagcttggg cacccagacc      240
tacatctgca acgtgaatca caagcccagc aacaccaagg tggacaagaa agttgagccc      300
aaatcttgtg acaaaactca cacatgccca ccgtgcccag cacctgaact cctgggggga      360
ccgtcagtct tcctcttacc cccaaaaccc aaggacaccc tcatgatctc ccggacccct      420
gaggtcacat gcgtggtggt ggacgtgagc cacgaagacc ctgaggtcaa gttcaactgg      480
tacgtggacg gcgtggaggt gcataatgcc aagacaaagc cgccggagga gcagtacaac      540
agcacgctcc gtgtggtcag cctcctcacc gtcctgcacc aggactggct gaatggcaag      600
gagtacaagt gcaaggtctc caacgcagcc ctcccagccc catcgcgaa aaccatctcc       660 aaagccaaag ggcagccccg agaaccacag gtgtacaccc tgcccccatc ccgggatgag      720
ctgaccaaga accaggtcag cctgacctgc ctggtcaaag gcttctatcc cagcgacatc      780
gccgtggagt gggagagcaa tgggcagccg gagaacaact acaagaccac gcctctcgtg      840
ctggactccg acggctcctt cttcctctac agcaagctca ccgtggacaa gagcaggtgg      900
cagcagggga acgtcttctc atgctccgtg atgcatgagg ctctgcacaa ccactacacg      960
cagaagagcc tctccctgtc tccgggtaaa                                      990
```

<210> SEQ ID NO 34
<211> LENGTH: 330
<212> TYPE: PRT
<213> ORGANISM: Artificial sequence
<220> FEATURE:
<223> OTHER INFORMATION: Fc34

<400> SEQUENCE: 34

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Leu Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Pro Glu
                165                 170                 175

Glu Gln Tyr Asn Ser Thr Leu Arg Val Val Ser Leu Leu Thr Val Leu
            180                 185                 190

His Gln Asp Trp Leu Asn Gly Lys Glu Tyr Lys Cys Lys Val Ser Asn
        195                 200                 205
```

```
Ala Ala Leu Pro Ala Pro Ile Glu Lys Thr Ile Ser Lys Ala Lys Gly
        210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Leu Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 35
<211> LENGTH: 990
<212> TYPE: DNA
<213> ORGANISM: Artificial sequence
<220> FEATURE:
<223> OTHER INFORMATION: Fc34

<400> SEQUENCE: 35

```
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtcgtgacc gtgccctcca gcagcttggg cacccagacc   240
tacatctgca acgtgaatca caagcccagc aacaccaagg tggacaagaa agttgagccc   300
aaatcttgtg acaaaactca cacatgccca ccgtgcccag cacctgaact cctgggggga   360
ccgtcagtct tcctcttacc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcggagga gcagtacaac   540
agcacgctcc gtgtggtcag cctcctcacc gtcctgcacc aggactggct gaatggcaag   600
gagtacaagt gcaaggtctc caacgcagcc ctcccagccc ccatcgagaa aaccatctcc   660
aaagccaaag ggcagccccg agaaccacag gtgtacaccc tgcccccatc ccgggatgag   720
ctgaccaaga accaggtcag cctgacctgc ctggtcaaag gcttctatcc cagcgacatc   780
gccgtggagt gggagagcaa tgggcagccg gagaacaact acaagaccac gcctctcgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa                                    990
```

<210> SEQ ID NO 36
<211> LENGTH: 330
<212> TYPE: PRT
<213> ORGANISM: Artificial sequence
<220> FEATURE:
<223> OTHER INFORMATION: Fc40

<400> SEQUENCE: 36

Ala Ser Thr Lys Gly Pro Ser Val Phe Pro Leu Ala Pro Ser Ser Lys

```
            1               5                  10                 15
          Ser Thr Ser Gly Gly Thr Ala Ala Leu Gly Cys Leu Val Lys Asp Tyr
                          20                  25                 30

Phe Pro Glu Pro Val Thr Val Ser Trp Asn Ser Gly Ala Leu Thr Ser
                          35                  40                  45

Gly Val His Thr Phe Pro Ala Val Leu Gln Ser Ser Gly Leu Tyr Ser
                   50                  55                  60

Leu Ser Ser Val Val Thr Val Pro Ser Ser Leu Gly Thr Gln Thr
          65                  70                  75                  80

Tyr Ile Cys Asn Val Asn His Lys Pro Ser Asn Thr Lys Val Asp Lys
                              85                  90                  95

Lys Val Glu Pro Lys Ser Cys Asp Lys Thr His Thr Cys Pro Pro Cys
                         100                 105                 110

Pro Ala Pro Glu Leu Leu Gly Gly Pro Ser Val Phe Leu Leu Pro Pro
                         115                 120                 125

Lys Pro Lys Asp Thr Leu Met Ile Ser Arg Thr Pro Glu Val Thr Cys
                    130                 135                 140

Val Val Val Asp Val Ser His Glu Asp Pro Glu Val Lys Phe Asn Trp
          145                 150                 155                 160

Tyr Val Asp Gly Val Glu Val His Asn Ala Lys Thr Lys Pro Arg Glu
                              165                 170                 175

Glu Gln Tyr Asn Ser Thr Leu Arg Val Val Ser Ile Leu Thr Val Leu
                         180                 185                 190

His Gln Asp Trp Leu Asn Gly Lys Glu Tyr Lys Cys Lys Val Ser Asn
                    195                 200                 205

Ala Ala Leu Pro Ala Pro Ile Glu Lys Thr Ile Ser Lys Ala Lys Gly
          210                 215                 220

Gln Pro Arg Glu Pro Gln Val Tyr Thr Leu Pro Pro Ser Arg Asp Glu
          225                 230                 235                 240

Leu Thr Lys Asn Gln Val Ser Leu Thr Cys Leu Val Lys Gly Phe Tyr
                              245                 250                 255

Pro Ser Asp Ile Ala Val Glu Trp Glu Ser Asn Gly Gln Pro Glu Asn
                         260                 265                 270

Asn Tyr Lys Thr Thr Pro Leu Val Leu Asp Ser Asp Gly Ser Phe Phe
                    275                 280                 285

Leu Tyr Ser Lys Leu Thr Val Asp Lys Ser Arg Trp Gln Gln Gly Asn
          290                 295                 300

Val Phe Ser Cys Ser Val Met His Glu Ala Leu His Asn His Tyr Thr
          305                 310                 315                 320

Gln Lys Ser Leu Ser Leu Ser Pro Gly Lys
                              325                 330

<210> SEQ ID NO 37
<211> LENGTH: 990
<212> TYPE: DNA
<213> ORGANISM: Artificial sequence
<220> FEATURE:
<223> OTHER INFORMATION: Fc40

<400> SEQUENCE: 37
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtcgtgacc gtgccctcca gcagcttggg cacccagacc     240
```

```
tacatctgca acgtgaatca caagcccagc aacaccaagg tggacaagaa agttgagccc      300
aaatcttgtg acaaaactca cacatgccca ccgtgcccag cacctgaact cctgggggga      360
ccgtcagtct tcctcttacc cccaaaaccc aaggacaccc tcatgatctc ccggacccct      420
gaggtcacat gcgtggtggt ggacgtgagc cacgaagacc ctgaggtcaa gttcaactgg      480
tacgtggacg gcgtggaggt gcataatgcc aagacaaagc cgccggagga gcagtacaac      540
agcacgctcc gtgtggtcag catcctcacc gtcctgcacc aggactggct gaatggcaag      600
gagtacaagt gcaaggtctc caacgcagcc ctcccagccc ccatcgagaa aaccatctcc      660
aaagccaaag gcagccccg  agaaccacag gtgtacaccc tgcccccatc ccgggatgag      720
ctgaccaaga accaggtcag cctgacctgc ctggtcaaag gcttctatcc cagcgacatc      780
gccgtggagt gggagagcaa tgggcagccg gagaacaact acaagaccac gcctctcgtg      840
ctggactccg acggctcctt cttcctctac agcaagctca ccgtggacaa gagcaggtgg      900
cagcagggga acgtcttctc atgctccgtg atgcatgagg ctctgcacaa ccactacacg      960
cagaagagcc tctccctgtc tccgggtaaa                                      990
```